United States Patent
LaMarr et al.

(10) Patent No.: US 8,414,774 B2
(45) Date of Patent: *Apr. 9, 2013

(54) SYSTEMS AND METHODS FOR HIGH-THROUGHPUT SCREENING OF FLUIDIC SAMPLES

(75) Inventors: William A. LaMarr, Andover, MA (US); Can C. Ozbal, Maynard, MA (US); Arrin Katz, Cambridge, MA (US); Donald Green, Watertown, MA (US)

(73) Assignee: Agilent Technologies, Inc., Santa Clara, CA (US)

( * ) Notice: Subject to any disclaimer, the term of this patent is extended or adjusted under 35 U.S.C. 154(b) by 663 days.

This patent is subject to a terminal disclaimer.

(21) Appl. No.: 12/560,324

(22) Filed: Sep. 15, 2009

(65) Prior Publication Data
US 2010/0024527 A1 Feb. 4, 2010

Related U.S. Application Data

(63) Continuation-in-part of application No. 11/063,252, filed on Feb. 22, 2005, now Pat. No. 7,588,725, which is a continuation-in-part of application No. 10/984,027, filed on Nov. 8, 2004, which is a continuation-in-part of application No. 10/267,912, filed on Oct. 8, 2002, now abandoned, which is a continuation-in-part of application No. 09/842,361, filed on Apr. 25, 2001, now abandoned, application No. 12/560,324, which is a continuation-in-part of application No. PCT/US2008/082229, filed on Nov. 3, 2008.

(60) Provisional application No. 60/518,240, filed on Nov. 7, 2003, provisional application No. 61/001,595, filed on Nov. 2, 2007, provisional application No. 61/001,597, filed on Nov. 2, 2007.

(51) Int. Cl.
*B01D 15/08* (2006.01)
*G01N 30/02* (2006.01)

(52) U.S. Cl. .... 210/656; 73/61.56; 210/141; 210/198.2; 422/70; 422/501; 422/509; 422/527; 422/537; 436/177; 436/180

(58) Field of Classification Search .................... 422/63, 422/64, 68.1, 69, 70, 100–104, 99, 501, 509, 422/513, 527, 537–539; 436/43, 52–54, 436/161, 174, 177–180; 210/141, 143, 198.2, 210/656, 659; 73/61.52–61.56, 863.31, 863.33, 73/863.85, 863.01, 864, 864.01
See application file for complete search history.

(56) References Cited

U.S. PATENT DOCUMENTS 3,301,065 A 1/1967 Jayetal et al.
3,524,305 A 8/1970 Ives
(Continued)

FOREIGN PATENT DOCUMENTS

EP 0556748 8/1993
EP 60022478 8/1993
(Continued)

OTHER PUBLICATIONS

Communication, European Patent Application No. EP 04 800 778.5-2204 (Feb. 14, 2008).
(Continued)

*Primary Examiner* — Joseph Drodge

(57) ABSTRACT

Aspects of the invention provide systems and methods for high-throughput screening of fluidic samples. In some embodiments, two chromatography columns are utilized in series. The first chromatography column can have a high affinity for phosphorylated compounds while the second chromatography column has a high affinity for one or more analytes of interest.

22 Claims, 26 Drawing Sheets

U.S. PATENT DOCUMENTS

| | | | |
|---|---|---|---|
| 3,559,458 A * | 2/1971 | Hrdina | 73/23.41 |
| 3,566,677 A | 3/1971 | Cole et al. | |
| 3,710,279 A | 1/1973 | Ashkin | |
| 3,734,622 A | 5/1973 | Adler | |
| 3,855,846 A | 12/1974 | Forget et al. | |
| 3,929,004 A | 12/1975 | Gunew et al. | |
| 3,997,298 A | 12/1976 | McLafferty et al. | |
| 4,055,987 A | 11/1977 | McFadden | |
| 4,071,315 A | 1/1978 | Chateau et al. | |
| 4,111,553 A | 9/1978 | Garnys | |
| 4,113,383 A | 9/1978 | Burns et al. | |
| 4,196,615 A | 4/1980 | Davis | |
| 4,458,066 A | 7/1984 | Caruthers et al. | |
| 4,568,875 A | 2/1986 | Piso et al. | |
| 4,659,677 A | 4/1987 | Glover et al. | |
| 4,837,160 A | 6/1989 | Meserol et al. | |
| 4,841,145 A | 6/1989 | Wada et al. | |
| 4,883,642 A | 11/1989 | Bisconte | |
| 4,913,821 A | 4/1990 | Melcher et al. | |
| 5,006,749 A | 4/1991 | White | |
| 5,071,547 A | 12/1991 | Cazer et al. | |
| 5,122,287 A | 6/1992 | Hsiung | |
| 5,191,212 A | 3/1993 | Falk et al. | |
| 5,334,837 A | 8/1994 | Ikeda et al. | |
| 5,462,660 A | 10/1995 | Singleton et al. | |
| 5,486,337 A | 1/1996 | Ohkawa | |
| 5,507,777 A | 4/1996 | Kus et al. | |
| 5,508,200 A | 4/1996 | Tiffany et al. | |
| 5,516,692 A | 5/1996 | Berndt | |
| 5,630,943 A | 5/1997 | Grill | |
| 5,643,628 A | 7/1997 | Sonderegger | |
| 5,739,422 A * | 4/1998 | Riviello et al. | 73/61.55 |
| 5,792,663 A | 8/1998 | Fry et al. | |
| 5,814,742 A | 9/1998 | Vissers et al. | |
| 5,855,851 A | 1/1999 | Matsubara et al. | |
| 5,882,601 A | 3/1999 | Kath et al. | |
| 5,885,529 A | 3/1999 | Babson et al. | |
| 5,906,223 A | 5/1999 | Pinkham | |
| 5,945,070 A | 8/1999 | Kath et al. | |
| 5,985,214 A | 11/1999 | Stylli et al. | |
| 6,019,897 A | 2/2000 | Horsman et al. | |
| 6,066,848 A | 5/2000 | Kassel et al. | |
| 6,123,849 A | 9/2000 | Purdom | |
| 6,149,818 A | 11/2000 | Nakamura et al. | |
| 6,149,882 A | 11/2000 | Guan et al. | |
| 6,150,172 A | 11/2000 | Schmerr et al. | |
| 6,175,409 B1 * | 1/2001 | Nielsen et al. | 506/12 |
| 6,296,771 B1 | 10/2001 | Miroslav | |
| 6,309,600 B1 | 10/2001 | Hunter | |
| 6,318,157 B1 | 11/2001 | Corso et al. | |
| 6,344,172 B1 | 2/2002 | Afeyan et al. | |
| 6,358,692 B1 | 3/2002 | Jindal et al. | |
| 6,387,257 B1 | 5/2002 | Hindsgaul et al. | |
| 6,416,663 B1 * | 7/2002 | Miroslav et al. | 210/198.2 |
| 6,423,536 B1 | 7/2002 | Jovanovich et al. | |
| 6,436,292 B1 | 8/2002 | Petro | |
| 6,461,515 B1 | 10/2002 | Safir et al. | |
| 6,592,822 B1 | 7/2003 | Chandler | |
| 6,656,739 B2 | 12/2003 | Hindsgaul et al. | |
| 6,787,111 B2 | 9/2004 | Roach et al. | |
| 6,812,030 B2 | 11/2004 | Ozbal et al. | |
| 6,813,568 B2 | 11/2004 | Powell et al. | |
| 6,863,362 B2 | 3/2005 | Reichel et al. | |
| 6,866,786 B2 | 3/2005 | Petro et al. | |
| 6,932,939 B2 | 8/2005 | Ozbal et al. | |
| 7,100,460 B2 | 9/2006 | Ozbal | |
| 7,189,504 B2 | 3/2007 | Marnett et al. | |
| 7,214,320 B1 | 5/2007 | Gregori et al. | |
| 7,225,079 B2 | 5/2007 | Gjerde et al. | |
| 7,303,727 B1 | 12/2007 | Dubrow et al. | |
| 7,329,353 B2 | 2/2008 | Dillon et al. | |
| 7,588,725 B2 * | 9/2009 | Ozbal et al. | 422/63 |
| 2002/0001544 A1 | 1/2002 | Hess et al. | |
| 2002/0019061 A1 | 2/2002 | Lai et al. | |
| 2002/0150926 A1 | 10/2002 | Jindal et al. | |
| 2003/0023585 A1 | 1/2003 | Castelli | |
| 2003/0106797 A1 | 6/2003 | Schneider et al. | |
| 2003/0119193 A1 | 6/2003 | Hess et al. | |
| 2004/0138106 A1 | 7/2004 | Schultz et al. | |
| 2004/0171085 A1 | 9/2004 | Joazeiro | |
| 2004/0198637 A1 | 10/2004 | Schultz et al. | |
| 2004/0235187 A1 | 11/2004 | LaCourse et al. | |
| 2005/0019755 A1 | 1/2005 | Marchessault et al. | |
| 2005/0053973 A1 | 3/2005 | Kolkman et al. | |
| 2005/0123970 A1 * | 6/2005 | Ozbal et al. | 435/6 |
| 2005/0136513 A1 | 6/2005 | Zhang et al. | |
| 2005/0194318 A1 | 9/2005 | Ozbal et al. | |
| 2006/0078471 A1 | 4/2006 | Witty et al. | |
| 2008/0093300 A1 | 4/2008 | Clarke et al. | |
| 2008/0115568 A1 | 5/2008 | Lee et al. | |

FOREIGN PATENT DOCUMENTS

| | | |
|---|---|---|
| EP | 0752281 | 1/1997 |
| EP | 0983788 | 3/2000 |
| FR | 2820058 | 8/2002 |
| JP | 10-332658 | 12/1998 |
| WO | WO-95/34374 | 12/1995 |
| WO | WO-98/08093 | 2/1998 |
| WO | WO-9815355 | 4/1998 |
| WO | WO-9911373 | 3/1999 |
| WO | WO-99/50667 | 10/1999 |
| WO | WO-0045929 | 8/2000 |
| WO | WO-00/63705 | 10/2000 |
| WO | WO-00/79238 | 12/2000 |
| WO | WO-02/25259 | 3/2002 |
| WO | 2005/048126 A2 | 5/2005 |
| WO | WO-2007059312 | 5/2007 |

OTHER PUBLICATIONS

International Preliminary Report on Patentability (IPER), International Application No. PCT/US2004/036885 (May 8, 2006).

Written Opinion of the International Searching Authority for PCT/US2004/036885.

Francis Beaudry et al., In Vivo Pharmacokinetic Screening in Cassette Dosing Experiments: the Use of On-Line Prospekt® Liquid Chromatography/Atmospheric Pressure Chemical Ionization Tandem Mass Spectrometry Technology in Drug Discovery', Rapid Commun. Mass Spectrom. 12, 1216-1222 (1998).

Kenneth J. Fountain et al., "Electrospray Ionization Mass Spectrometric Analysis of Nucleic Acids Using High-Throughput On-Line Desalting", Rapid Commun. Mass Spectrom. 18, 1295-1302 (2004).

A. Goraczko et al., "A Six-Volume Rotary Injection Valve for High Performance Liquid Chromatography", Journal of High Resolution Chromatography & Chromatography Communications, vol. 9, 61-63 (Jan. 1986).

Robert L. St. Claire, III, "Positive Ion Electrospray Ionization Tandem Mass Spectrospray Coupled to Ion-Pairing High-Performance Liquid Chromatography with a Phosphate Buffer for the Quantitative Analysis of Intrcellular Nucletides", Rapid Commun. Mass Spectrum. 14, 1625-1634 (2000).

Waters Corporation, MassPREP™ On-Line Desalting Cartridge Care and Use Manual 1-5 (Sep. 2007).

Mike S. Lee & Edward H. Kerns, "LC/MS Applications in Drug Development", Mass Spectrometry Reviews, 18, 187-279 (1999).

Weng Naidong et al., "Liquid Chromatography/Tandem Mass Spectrometric Bioanalysis Using Normal -Phase Columns with Aqueous/Organic Mobile Phases—a Novel Approach of Eliminating Evaporation and Reconstitution Steps in 96-Well SPE", Rapid Commun. Mass Spectrom. 16, 1965-1975 (2002).

Optek Technology, Press Release, "Optek's Non-Contact Fluid Sensor Detects Liquid Through Transparent Tubing", (Mar. 18, 2004).

Schowchien Hsieh et al., "Increasing Throughput of Parallel On-Line Extraction Liquid Chromatography/Electrospray Ionization Tandem Mass Spectrometry System for GLP Quantitative Bioanalysis in Drug Development," 18 Rapid Commun. Mass Spectrom. 285-92 (2004).

R.E. Lovins et al., "Liquid Chromatography-Mass Spectrometry: Coupling of a Liquid Chromatograph to a Mass Spectrometer," 45(8) Analytical Chem. 1553-56 (1973).

Gustaf Hulthe et al., "Coupling of Open Tublar Liquid Chromatography to Electrospray Mass Spectrometry with a Nanospray Interface," 71(14) Analytical Chem. 2915-21 (1999).

Yufeng Shen et al., "High Efficiency Nanoscale Liquid Chromatography Coupled On-Line with Mass Spectrometry Using Nanoelectrospray Ionization for Proteins," 74(16) Analytical Chem., 4235-49 (2002).

Notice of Reasons for Rejection, Japanese Patent Application No. JP 2006-539662 (Nov. 18, 2009).

W.M.A. Niessen, "Advances in instrumentation in liquid chromatography-mass spectrometry and related liquid-introduction techniques", Journal of Chromatography A 794 (1998) 407-435.

Lyndon A. Ellis & David J. Roberts, "Chromatographic & hyphenated methods for elemental speciation in environmental media," 774 J. Chromatography A. 3-19 (1997).

R.M. Holt et al., "High-performance Liquid Chromatography/NMR Spectrometry/Mass Spectrometry/Mass Spectrometry: Further Advances in Hyphenated Technology," 32 J. Mass Spectrometry 64-70 (1997).

Charles L. Wilkins, "Hyphenated Techniques for Analysis of Complex Organic Mixtures," 222 Science 291-96 (1983).

Jean-Luc Wolfender, et al., "The Potential of LC-NMR in Phytochemical Analysis," 12 Phytochem. Anal. 2-22 (2001).

International Search Report, International Application No. PCT/US2004/036885 (Jun. 7, 2005).

J.A. Pascual, et al., "Development of a precolumn capillary liquid chromatography switching system for coupling to mass spectrometry", Journal of Microcolumn Separations, 1996, 8:383-87.

* cited by examiner

SYSTEMS AND METHODS FOR HIGH-THROUGHPUT SCREENING OF FLUIDIC SAMPLES

CROSS REFERENCE TO RELATED APPLICATIONS

This application is a continuation-in-part of International Application No. PCT/US2008/082229, filed Nov. 3, 2008, which claims priority to U.S. Provisional Patent Application Ser. No. 61/001,595, filed Nov. 2, 2007 and which also claims priority to U.S. Provisional Patent Application Ser. No. 61/001,597, filed Nov. 2, 2007. This application is also a continuation in part of U.S. patent application Ser. No. 11/063,252, filed Feb. 2, 2005 and issued as U.S. Pat. No. 7,588,725, which is a continuation-in-part of U.S. patent application Ser. No. 10/984,027, filed, Nov. 8, 2004, which claims priority to U.S. Provisional Patent Application Ser. No. 60/518,240, filed Nov. 7, 2003, and is also a continuation-in-part of U.S. patent application Ser. No. 10/267,912, filed Oct. 8, 2002 and now abandoned, which is a continuation-in-part of U.S. patent application Ser. No. 09/842,361, filed Apr. 25, 2001 and now abandoned. Each of these patent applications is hereby incorporated by reference in its entirety.

BACKGROUND

Important functions in the field of drug discovery, known as pharmacokinetics and pharmacodynamics (PK and PD), involve the quantification of one or more test compounds in a biological sample such as plasma, urine, cerebrospinal fluid (CSF), or similar. In the discovery or early development phases of creating new pharmacological compounds, PK and PD experiments typically involve dosing a test animal and monitoring the level of the test compound and/or its metabolites in various biological fluids or tissues as a function of time.

A common method for the quantification of test compounds in biological samples involves the use of a radioisotope of the test compound. The concentration of the test compound can be measured by tracking the amount of radioactivity present in each sample. However, often a radioisotope of the test compound of interest is not available. In such cases mass spectrometry (MS) is commonly used as the analytical method for the quantification of test compounds. MS is a powerful technique that can be used to selectively and quantitatively detect one or more analytes of interest in a complex mixture based on the molecular mass of those analytes.

While MS is a very powerful technique that is commonly used in many areas of the drug discovery process, it has certain limitations. One requirement for MS is that the analytes, typically in liquid phase, to be detected need to be ionized and fully desolvated to enter the MS inlet and reach the detector. There are several commonly used methods for ionizing and desolvating samples including electrospray ionization (ESI), atmospheric pressure chemical ionization (APCI) and atmospheric pressure photo ionization (APPI). These methods are often collectively called atmospheric pressure ionization (API). In all API methods, the samples are ionized through the application of a strong electric field that is typically many thousands of volts in magnitude. Often a heated inert gas, such as nitrogen, is applied to evaporate the solvent associated with the sample resulting in an analyte that is ionized and is in the gas phase.

Unfortunately, this approach of sample ionization does not work well for samples that contain high levels of ions, such as salts and/or buffers. In samples that contain high levels of ions, a phenomenon known as ion suppression occurs, in which the bulk of the ionization occurs within the salt or buffer molecules and little or no analyte of interest is actually ionized. The result is that the sensitivity of the MS technique is dramatically reduced when such samples are analyzed. Furthermore, most salts and buffer are not volatile and, when desolvated in an API MS instrument, tend to precipitate in the source region of the instrument and often cause a further decline in instrument performance.

To overcome the problems of ion suppression samples to be analyzed are generally purified and/or fractionated prior to MS analysis by some form of chromatography. In general, there are two major forms of sample preparation in MS analysis that can be described as on-line techniques and decoupled techniques. In decoupled techniques, the samples are purified off-line in a separate step such as solid-phase extraction (SPE) or liquid-liquid extraction (LLE). Often, many samples are purified together in parallel to provide an increase in throughput. On-line techniques are also sometimes described as "hyphenated" methods and involve coupling some form of chromatography system, such as liquid chromatography (LC) directly with the mass spectrometer such that the eluate from the chromatography system in analyzed by the MS. Often, high-pressure liquid chromatography (HPLC) is interfaced with the MS in a technique known as HPLC-MS.

Although HPLC-MS is an immensely powerful technique for biological analysis, it is limited by a relatively slow throughput, which is typically on the order of several minutes per sample. In cases where a large number of samples must be analyzed, the bioanalysis using HPLC-MS can create a significant bottleneck. While various methods have been described for increasing the throughput of the HPLC-MS process, including multiplexing of a plurality of HPLC system to a single MS or decreasing the run times of HPLC systems through the use of smaller particles or a ballistic gradient, most commercially available systems still require more than 1 minute per sample. The RAPIDFIRE® system by BioTrove, Inc. of Woburn, Mass. uses a miniaturized and fully automated on-line solid-phase extraction system coupled to a mass spectrometer (SPE-MS) and has been shown to facilitate MS analysis at throughputs up to 6 seconds per sample for a wide range of applications including high-throughput screening and in vitro ADME (related RF patents should be referenced).

PK and PD analysis, particularly from plasma samples, create a significant challenge for an SPE-MS system due to the limited sample fractionation afforded by the SPE step. While very effective at removing salts and buffers, the SPE method does little or no fractionation of other compounds in the sample. In complex biological samples such as plasma, this could translate to a very large number of compounds at high concentrations that can cause significant ion suppression.

In the case of plasma samples there are typically two major issues that must be overcome. The first is a high concentration of proteins, notably serum albumin, which can be found at concentrations as high as 20 mg/mL. At these concentrations proteins tend to precipitate in organic solvents, such as acetonitrile and methyl alcohol, which are commonly used to elute the analytes from the SPE columns creating the physical challenge of clogging as well as ion suppression. Fortunately, removing proteins from samples can be achieved very quickly and simply with a variety of techniques which are well known to those skilled in the practice.

A bigger challenge for the analysis of PK/PD samples using SPE-MS techniques is the presence of millimolar concentrations of a wide range of phospholipids in plasma. These phospholipids are typically retained on the standard reversed-phase solid-phase extraction systems that are routinely used in most SPE-MS applications. The result is that the phospholipids co-purify with the analytes of interest and generally result in significant ion suppression. Typically, due to the effects of phospholipid ion-suppression, the lower limit of quantification (LLQ) of an analyte of interest for a SPE-MS method does not compare with that of an HPLC-MS method where the analyte of interest is fractionated and separated from the phospholipids.

Accordingly, there is a need for systems and methods the enable the use of SPE-MS methods for high-throughput PK/PD analysis of plasma samples while achieving limits of quantification that are comparable to HPLC-MS methods.

SUMMARY OF THE INVENTION

One embodiment of the invention provides an auto-injection system for high throughput screening of fluidic samples. The system includes: a sample injection valve having a first position that applies a reduced pressure to a sample sipper tube for aspirating a fluidic sample into the sample sipper tube and a second position that delivers the fluidic sample to a sample supply loop; a first column control valve in fluid communication with a first chromatography column, said first column control valve having a first position that delivers the fluidic sample from the sample supply loop to said first chromatography column in a first direction and a second position that flows a first elution solvent over said first chromatography column in a second direction; and a second column control valve in fluid communication with a sample analyzer and a second chromatography column, and configured to facilitate a continuous flow of a second elution solvent to the sample analyzer, said second column control valve having a first position that simultaneously delivers the fluidic sample from the sample supply loop to said second chromatography column in said first direction and delivers the second elution solvent to the sample analyzer and a second position that flows the second elution solvent over said second chromatography column in a second direction to deliver the fluidic sample and the elution solvent to the sample analyzer.

This aspect of the invention can have a variety of embodiments. In one embodiment, the sample analyzer is a mass spectrometry device. The first chromatography column can include a chromatography matrix selected from the group consisting of: silica gel, titanium oxide matrix, and zirconium oxide matrix. The second chromatography column can be selected from the group consisting of: an ion exchange chromatography column, a cation exchange chromatography column, a hydrophilic interaction chromatography column, and a size exclusion chromatography column.

The system can include an optical detector for analyzing the sample from the second chromatography column. The system can include a diversion valve located between the second chromatography column and the sample analyzer. The diversion valve can be configured for actuation in response to a signal generated by the optical detector. The system can include a fraction collector.

The first elution solvent, the second elution solvent, and the third elution solvent can be polar solvents. The first elution solvent, the second elution solvent, and the third elution solvent can be non-polar solvents.

The first position of the first column control valve can supply wash buffer solution to wash the first chromatography column.

Another aspect of the invention provides an auto-injection system for high throughput screening of fluidic samples. The system includes: a sample injection valve coupled to a sipper, a vacuum, and a sample loop; a wash control valve coupled to the sample injection valve, a first column control valve, a wash buffer solution pump, and a first elution solvent pump; a first column control valve coupled to the sample injection valve, a second elution solvent pump, a first chromatography column, and a second column control valve; and a second column control valve coupled to the first column control valve, a third elution solvent pump, a second chromatography column, and a sample analyzer. The sample injection valve is configured for actuation to: a first position, wherein the sample loop is in communication with the vacuum and the sipper to load a sample and a second position, wherein the sample loop is in communication with the wash control valve and the first column control valve. The first column control valve is configured for actuation to: a first position, wherein the first chromatography column is in communication with the sample injection valve to deliver the sample to the chromatography column in a first direction and a second position, wherein the first chromatography column is in communication with the second elution solvent pump elute the first chromatography column. The second column control valve is configured to facilitate a continuous flow of an elution solvent to the second column control valve by actuation to: a first position, wherein the second chromatography column is in communication with the first chromatography column via the first column control valve to deliver the unbound contents of said sample to the second chromatography column in a first direction and a second position, wherein the second chromatography column is in communication with the third elution solvent pump to flow a third elution solvent over the second chromatography column in a second direction and present the elution solvent and an eluted sample to the sample analyzer. The wash control valve is configured for actuation to: a first position, wherein the wash solvent pump is in communication with the sample injection valve and a second position, wherein the first elution pump is in communication with the sample injection valve.

Another aspect of the invention provides a method of preparing a sample containing phospholipid, a phosphopeptide, or a mixture thereof for analysis by a mass spectrometry device, the method comprising the use of the sample injection systems described herein.

This aspect can have a variety of embodiments. In one embodiment, the sample includes salt, buffer, or a mixture thereof.

Another aspect of the invention provides a method for high throughput screening of fluidic samples. The method includes: providing a system including a sample injection valve, a first column control valve, and a second column control valve wherein the sample injection valve is actuatable to a first position that applies a reduced pressure to a sample sipper tube for aspirating a fluidic sample into the sample sipper tube and a second position that delivers the fluidic sample to a sample supply loop, wherein the first column control valve is in fluid communication with a first chromatography column and the first column control valve having a first position that delivers the fluidic sample from the sample supply loop to said first chromatography column in a first direction and a second position that flows a first elution solvent over said first chromatography column in a second direction, and wherein the second column control valve is in fluid communication with a sample analyzer and a second chromatography column, and is configured to facilitate a continuous flow of a second elution solvent to the sample analyzer, the second column control valve having a first position that simultaneously delivers the fluidic sample from the sample supply loop to said second chromatography column in said first direction and delivers the second elution solvent to the sample analyzer and a second position that flows the second elution solvent over said second chromatography column in a second direction to deliver the fluidic sample and the elution solvent to the sample analyzer; actuating the sample injection valve, the first column control valve, and second column control valve to their first positions; actuating the sample injection valve to the second position; and actuating the first column control valve and the second column control valve to their second positions.

This aspect can have a variety of embodiments. In one embodiment, the method includes repeating the actuating steps in a cycle. The cycle can be performed at a speed of greater than two samples per minute. The sample analyzer can be a mass spectrometer. The sample can contain a phospholipid, a phosphopeptide, or a mixture thereof. The first chromatography column can have a chromatography matrix selected from the group consisting of: silica gel, titanium oxide matrix, and zirconium oxide matrix. The method can include preparing the sample by protein precipitation. The protein precipitation can be performed by adding trichloroacetic acid (100% w/v) to a sample to a concentration of 20% (v/v).

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments, an automated system and method for increasing sample throughput and/or analysis of selected components in complex biological, chemical, or environmental matrices is presented. Generally, the system includes a chromatography column and fluidic circuit that is capable of rapidly outputting a plurality of samples to an analyzer, such as a mass spectrometer. In various embodiments, sample throughput rates ranging from 30 seconds per sample to 1 second per sample or faster are achievable, depending on the specific application. Further embodiments of the invention include an auto-injection system that increases throughput and minimizes sample carryover. Details are discussed below.

Figure 1:
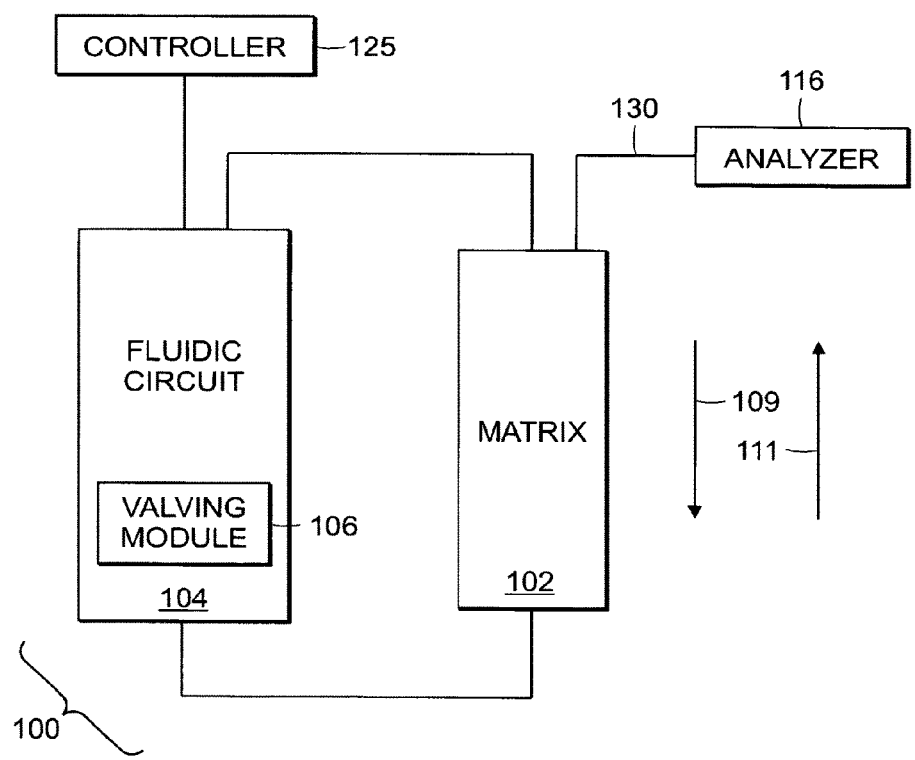
FIG. 1 is a block diagram of a rapid chromatography system, in accordance with an embodiment of the invention.

FIG. 1 shows a block diagram of a rapid chromatography system 100 for rapidly outputting an analyte of interest while removing undesirable salts, buffers, and other components from a complex mixture, in accordance with one embodiment of the invention. Such undesirable components may, for example, degrade analyzer performance or cause an output signal from an analyzer to be suppressed.

The system 100 relies on the principle of back-elution for the specific purpose of increasing sample throughput. In particular, the complex mixture to be analyzed is delivered to an insoluble matrix 102 in a first direction 109 via a fluidic circuit 104. The matrix 102, which may be packed in a chromatography column, is selected such that the analyte(s) of interest is selectively immobilized. The matrix 102 may be, without limitation, various resins known in the art of chromatography. Typically, the analyte binds to the first part of the matrix 102 encountered due to a phenomenon known as focusing. In focusing, a large amount of the analyte may be immobilized in a very small physical space within the head of the matrix 102 due to a strong affinity for that matrix 102.

Non-binding components of the complex mixture, which may include, without limitation, salts, buffers, and/or detergents, are not so immobilized and pass through the insoluble matrix 102. These undesirable components are typically diverted to waste by the fluidic circuit 104. To ensure sufficient removal of the undesirable components, the matrix 102 may be washed for a predetermined period of time, while the analyte(s) of interest is still immobilized and focused on the head of the matrix.

Once the undesirable components have been removed from the matrix, elution fluid is passed via the fluidic circuit 104 over the matrix 102 such that the analyte(s) is no longer immobilized by the matrix 102. However, instead of passing the elution fluid over the matrix 102 in the first direction 109, the elution fluid is passed over the matrix 102 in a second direction 111 that is substantially opposite the first direction 109, in accordance with preferred embodiments of the invention. Thus, the analyte(s) does not travel through the length of the matrix 102, but is instead back-eluted from the matrix 102 in the opposite direction it was loaded. Due to the focusing effect, the analyte(s) does not have to travel through the entire bed of the chromatography matrix 102, and a minimal amount of linear diffusion takes place. Thus, a sharp, concentrated sample peak can be output from the matrix 102 within a minimal bandwidth of time. The sharp sample peak obtained by back-elution is significantly sharper than those obtained when using conventional chromatography. The samples back-eluted from the matrix 102, which contain the analyte(s) of interest, can subsequently be introduced into an analyzer 116 in a rapid and concentrated manner.

In various embodiments of the invention, a controller 125 automatically controls the fluidic circuit 104 to periodically perform the steps of passing the fluid over the matrix 102 in the first direction and back-eluting the elution fluid over the matrix 102 in the second direction, so as to obtain a high sample-throughput rate. The controller 125 may include, without limitation, a processor which may be appropriately pre-programmed or configured to be loaded with an appropriate program. The controller 125 may work in conjunction with a robotic system that samples an aliquot of the complex mixture to be analyzed, and that allows for sequential presentation of each complex mixture to be analyzed.

Various methodologies may be used in which containers of each complex mixture to be analyzed and a sipper tube can be moved relative to one another to allow for sequential sampling. These methodologies include, but are not limited to, systems in which the containers of the liquid to be analyzed (e.g., a microtiter plate or an array of vials) are held in a fixed position and the sipper tube is translocated by means of a robotic arm to sequentially sample each container. Robotic microplate positioning systems are known in the art as in U.S. Pat. No. 5,985,214. Preferably, the robotic system should be capable of presenting samples at a rate that does not limit the throughput of the device. In other embodiments, the sipper tube can be immobilized and each container to be analyzed can be moved into a position where an aliquot can be sampled. In an embodiment, liquid samples can be transported to the sipper tube with the use of a laminated tape or belt system for sequential analysis, as described in the following U.S. patents and patent applications: U.S. Patent Application Publication No. 2002/0001544, U.S. Patent Application Publication No. 2003/0119193, and U.S. Pat. No. 6,812,030. Systems that incorporate elements of both approaches (e.g., moving the sample containers in two dimensions and the sipper tube in one dimension) are also possible.

The fluidic circuit 104 may include a valving module 106 that is capable of alternately directing fluid over the matrix in the first direction and back-eluting the elution fluid over the matrix in the second direction. Valving module 106 may include one or more valves. For example, FIGS. 2(a)-(c) are schematics of a chromatography system 200 that includes a chromatography matrix 225 and two injection valves 206 and 207, in accordance with one embodiment of the invention.

Figure 2A:
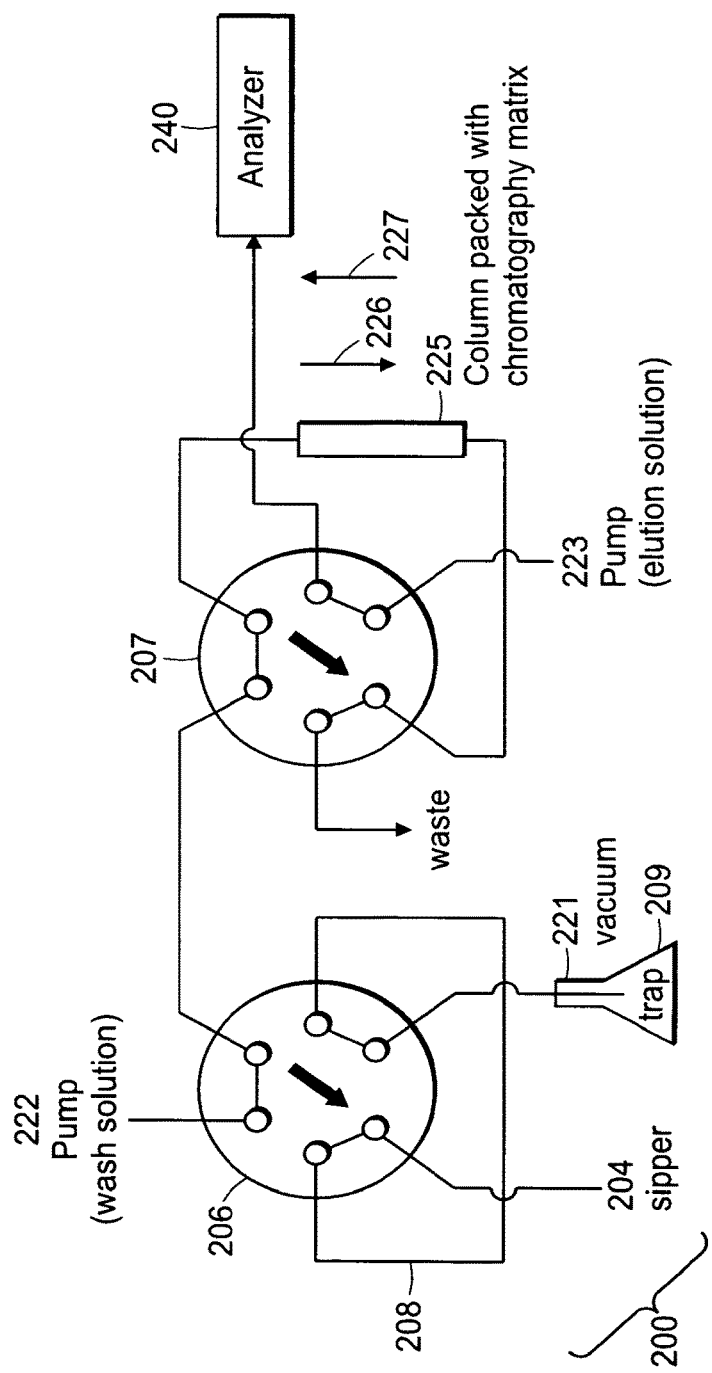
FIG. 2(a) is a schematic of a rapid chromatography system that includes two injection valves, in accordance with an embodiment of the invention.

FIG. 2(a) shows the position of the valves 206 and 207 when the complex mixture is being loaded into a sample loop 208. A reduced pressure 221 and an increased pressure 222 are continuously applied, by pumps, for example, to a first port and a second of port of the valve 206. The reduced pressure 221 is used to aspirate the complex mixture via a sipper tube 204. The sipper tube 204 may be, without limitation, narrow-bore capillary tubing. Enough of the complex mixture to fill sample loop 208 with a defined volume is aspirated. The amount of complex mixture to be passed over the matrix 225 can thus be controlled by the size of the sample loop 208. Any excess mixture aspirated is collected in a trap 209 that may be positioned, for example, between the injection valve 206 and the reduced pressure source 221.

In various embodiments, a wash solvent or buffer solution is positioned between the region of increased pressure 222 and the injection valve 206. While the complex mixture is being loaded into the sample loop 206, the increased pressure 222 applied to valve 206 pumps wash fluid to valve 207, which passes the wash fluid through the matrix 225 in a first direction 226. The output of the matrix 225 is diverted to waste by the valve 207. Additionally, an increased pressure 223 continuously applied to valve 207 pumps elution fluid, which may be positioned between the region of increased pressure 223 and valve 207, to an analyzer 240. In this manner, carryover from previous complex mixture/samples is flushed from the matrix 225 and the analyzer 240 while the complex mixture is being loaded into the sample loop 206.

Figure 2B:
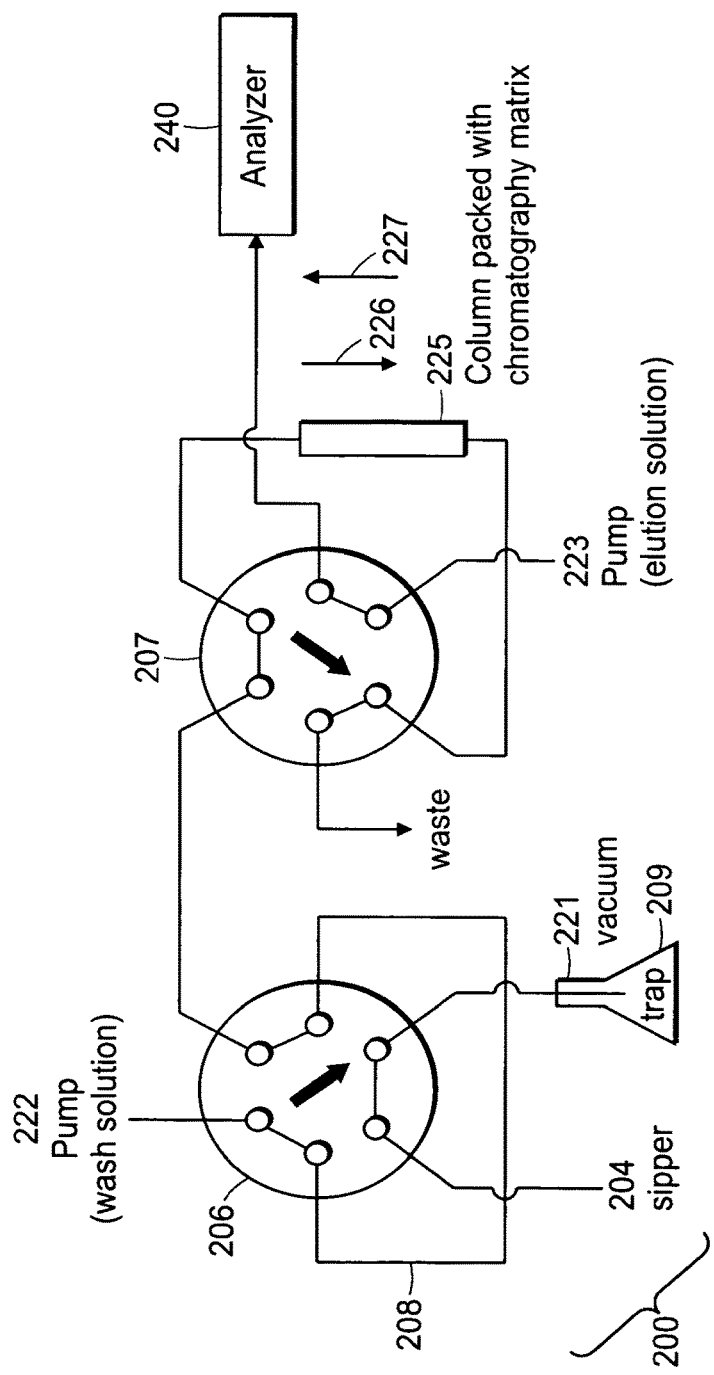
FIG. 2(b) is a schematic of the rapid chromatography system of FIG. 2(a) when a complex mixture is passed through a matrix in a first direction, in accordance with an embodiment of the invention.
Figure 2C:
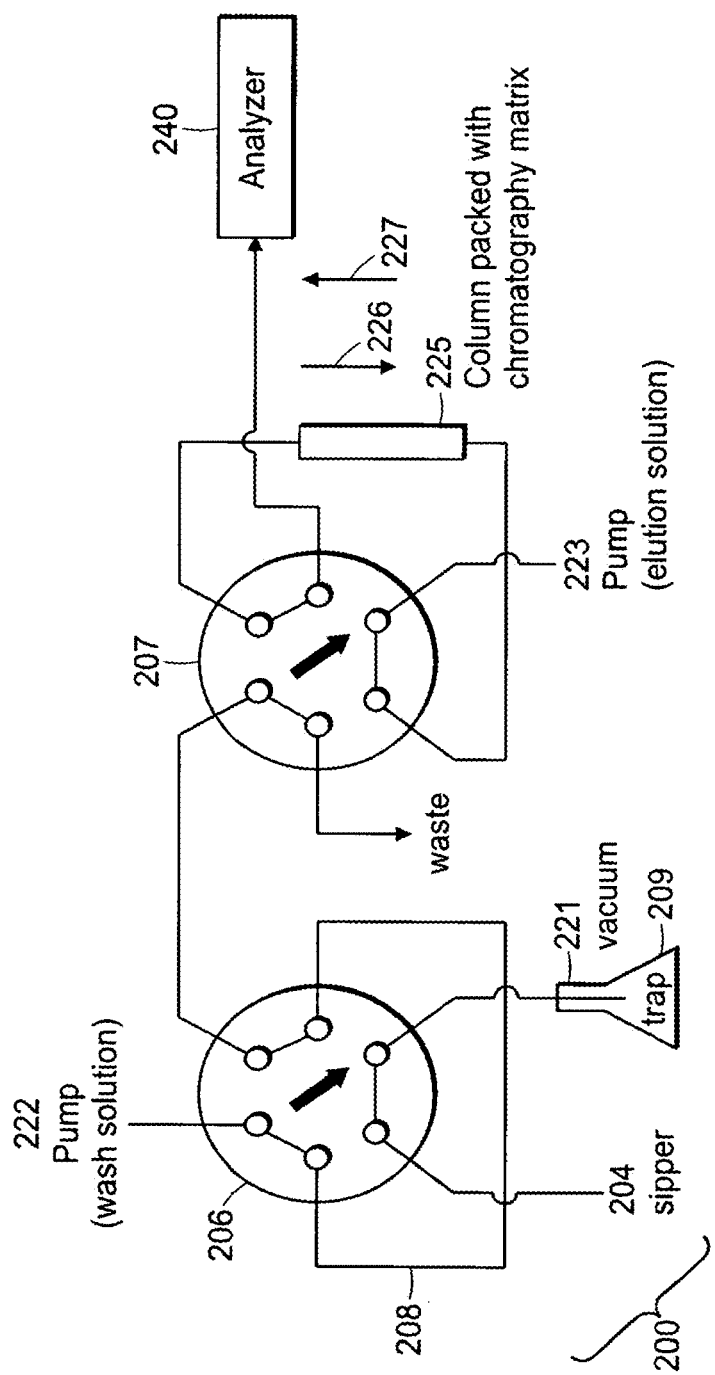
FIG. 2(c) is a schematic of the rapid chromatography system of FIG. 2(a) when elution fluid is passed through the matrix in a second direction, in accordance with an embodiment of the invention.

FIG. 2(b) shows the position of the valves 206 and 207 when the metered complex mixture from the sample loop 206 is passed through the matrix 225, in accordance with one embodiment of the invention. Upon actuation of the injection valve 206, the complex mixture, followed by wash fluid, is passed through the matrix 225 in the first direction 226. Due to the focusing effect, the analyte of interest binds to the first part of the matrix 225, as discussed above. The wash fluid that follows the sample ensures sufficient removal of the undesirable components (e.g. salts, buffers, detergents, etc.) from the matrix 225, which are diverted to waste. To clean the sipper tube 204 prior to aspiration of the next sample loop of complex mixture, the sipper tube 104 is dipped into a wash solvent or buffer solution. The reduced pressure 221 applied to the sipper tube 104 passes wash solvent through the sipper tube 204 and into trap 209.

After the analyte(s) of interest has been loaded onto the matrix 225 and the undesirable components removed, the valves 206 and 207 divert the pumping system that loads the complex mixture onto the matrix 225 away from the head of the matrix 225. Simultaneously, an elution fluid is passed through the matrix 225 in substantially the opposite direction 227 from which the complex mixture was loaded. The elution fluid, which may be either a solution or a solvent, dissociates the bound analyte(s) of interest from the matrix 225. In various embodiments, separate pumping systems are used to load the complex mixture, and pump the elution fluid across, the matrix 225.

FIG. 2(c) shows the position of the valves 206 and 207 when elution fluid is back-eluted through the matrix 225, in accordance with one embodiment of the invention. Valve 207 is actuated to pass the elution fluid to the matrix 225 in the second direction 227. Since the analyte is primarily immobilized within the head 226 of the matrix 225 due to the focusing effect, and does not have to travel the entire length of the matrix 225, thus limiting diffusion, the sample output of the matrix is delivered to the analyzer 240 in a concentrated manner within a small bandwidth of time. While back-eluting, wash solution is passed through the sample loop 206 to clean and prepare the sample loop 206 for subsequent aspiration of complex mixture.

The analyzer 240 may be, for example, an optical interrogator or mass spectrometer. In various embodiments, the sample may be presented directly to a mass spectrometer using a variety of standard systems, including atmospheric pressure chemical ionization (APCI), electrospray ionization (ESI) or atmospheric pressure photoionization (APPI). The mass spectrometer is capable of quantitatively analyzing a large number of compounds based on the mass-to-charge ratio of each compound. Further separation of individual compounds is generally not necessary, since an accurate mass-selective detection and quantification can be performed by mass spectrometry. The output of the MS is analyzed and the amount of compound present in the sample is determined by integrating the area under the MS peak.

After back-eluting, both valves 206 and 207 are actuated as shown in FIG. 2(a). The steps of loading the complex mixture into the sample loop 208 (if implemented), passing the complex mixture over the matrix 225 in the first direction, and back-eluting the elution fluid over the matrix 225 in the second direction are then periodically repeated so as to achieve a high sample-throughput rate.

Minimizing Peak Width of Matrix Sample Output

The sample peak width (at half height) at the output of the matrix 225 can be further minimized by selecting appropriate flow rates from the pumping systems 221, 222, and 223 and by selecting tubing diameters that further minimize linear diffusion as the complex mixture and samples are moved through the fluidic circuit 104. Typically, narrower bore tubing produces sharper peaks enabling higher throughput, but also lead to higher back-pressure in the fluidic pumping system. Similarly, higher flow rates also generally result in sharper peaks, but also lead to higher back-pressure. High flow rates can also lead to decreased signal intensity in a mass spectrometer due to incomplete sample ionization. Determining the maximum throughput of the system is therefore a compromise between several factors that can be modeled or determined empirically. The various parameters used, including the nature and type of the insoluble matrix, pumping flow rates and pressures, tubing specifications, the nature of the fluids used to perform the rapid chromatography, and the timing of the switching of the fluidic valves 206 and 207 must be optimized for each family of chemical compounds to be analyzed. This set of optimized parameters makes up a compound-specific method for high throughput mass spectrometric analysis. In accordance with various embodiments of the invention, typical ranges for tubing diameters range from 20 µm to 300 µm and flow rates range from 0.1 mL/min to 5 mL/min resulting in backpressures than may reach anywhere from 5 to 6000 psi.

Minimizing Carryover

A major concern in maximizing sample throughput is the elimination of sample-to-sample carryover. Referring back to FIG. 1, any sample that is not removed from the fluidic circuit 104, matrix 102, and analyzer interface 130 after one analysis may cause interference with the next sample. If a sample with a low level of analyte is preceded by a sample with a high level of analyte, carryover from the first sample may result in an incorrect analysis in the second, low analyte sample. Minimizing carryover is typically achieved by washing the fluidic circuit 104, matrix 102, and analyzer interface 130 with a solvent that fully solubilizes the analytes of interest so that they are removed from the system 100. Various embodiments of the invention also use this technique, and the fluidic circuit 104, matrix 102, and analyzer interface 130 may be flushed with the elution buffer/wash solution to minimize sample carryover.

Washing of the fluidic circuit 104 and other components of the system 100 which contact the complex mixture and/or sample is conventionally a time consuming step and a long washing step between samples limits the overall throughput of the system. Therefore, a system that requires a minimum amount of washing while producing an acceptably low level of carryover is highly desirable. This requirement can be achieved, in part, by making those surfaces in the fluidic circuit 104 and other components in the system 100 which contact the complex mixture and/or sample (including the sample loop 206, valving module 106, MS interface 130, etc.) bio-inert so as to minimize the amount of carryover and ease cleaning. Furthermore, due to the high backpressures generated by the pumping system, such surfaces must have a strong mechanical resistance and the ability to resist high pressure liquids without leaks.

A commonly used material for such systems is Poly Ether Ether Ketone (PEEK) that has strong chemical resistance and can be manufactured in a wide range of interior and exterior diameters. However, in preferred embodiments of the invention, the tubing within the fluidic circuit 104 is manufactured from polyimide. Polyimide tubing has exceptionally low carryover of even very highly hydrophobic compounds, can resist high pressures before failing and can be manufactured in the 20-300 micrometer inner diameters that are optimum for minimizing linear diffusion. Use of a polyimide fluidic system allows for very rapid washing steps between samples for a wide range of analytes with minimal carryover. Another option for the construction of the fluidic circuit 104 and other components which contact the complex mixture and/or sample is titanium or titanium alloys that are also known to have low carryover properties. The fluidic circuit 104 may also include a microfluidic biochip that may have, without limitation, channels having a diameter between 20 µm to 300 µm optimized for minimal linear diffusion.

Another embodiment of the invention is to construct the fluidic pathway in full or in part from a material such as stainless steel. Stainless steel is not a particularly bio-inert substrate and tends to strongly adsorb hydrophobic compounds in its surface. However, the surfaces of the fluidic circuit 104 and other components which contact the complex mixture and/or sample may be chemically or physically coated with a hydrophobic or hydrophilic film (e.g., Teflon, polyethylene glycol) by methods known to those familiar to the art in a manner that will minimize the binding of analyte(s), thus minimizing carryover.

Fluidic Valves

In accordance with various embodiments of the invention, fluidic valves in the fluidic circuit 104 are actuated to reverse direction of flow across the chromatography matrix 102. Typically, the flow across the matrix 102 needs to be reversed twice for each sample output from the matrix 102. The complex mixture 102 is first loaded onto the matrix 102 in one direction and the analyte(s) are bound but other components (e.g. salts, buffers, detergents, etc.) are not. The flow is then reversed and the analyte(s) are eluted off of the matrix 102 in the opposite direction to which there were loaded and diverted to the analyzer 116 for analysis. Finally, the flow is reversed again in preparation for the next sample. In many fluidic valves used in such microfluidic applications, the flow of liquid through the valve is physically stopped during the time at which the valve is being actuated. Typical electronically actuated valve modules 106 can switch between states in 100 milliseconds or slower. Pneumatically actuated valves may be switched much faster, and may reach actuation times of 30 to 40 milliseconds. This short blockage of flow during the actuation time is not a concern during conventional LC where runs typically last minutes.

However, the blockage of flow becomes a concern at very high throughput rates where the sample throughput time approaches 1 sample/second. Typically, the injection valves that may be used in this system allow for fluidic communication between two ports and have two actuation positions. However, if the valve is adjusted to an intermediate state between the actuation positions, the fluid communication is physically cut and no fluid can pass through the valve. During the actuation procedure there is a finite amount of time as the valve is rotated from one position to the other that the flow of fluid through the valve is cut. The high-pressure pumps that are pushing fluid through the valves continue to operate during this time. The creation of a blockage in flow at the valve during the actuation process results in an increase in the pressure within the fluidic circuit between the valve and the high-pressure pump. If the pressure increase is large enough it will eventually result in a failure of the fluidic system and could result in a leak. With conventional valves systems, the pressure increase is transient and the increase in pressure is not sufficient to actually cause a failure of the fluidic circuit. However, the blockage in the flow will be observed in the baseline of the mass spectrometer signal. Since the impurities in the solvent that result in the background MS signal are eliminated with a blockage in flow, the baseline tends to drop significantly during the valve actuation. When the valve has finished rotating and a fluidic connection is reestablished, the increased pressure between the pump and the valve is released and a higher than normal flow of solvent is delivered to the mass spectrometer. This results in an increased amount of impurities entering the mass spectrometer and an increase in the background signal. If this event overlaps with analyte signal it can lead to unsymmetrical peaks, distorted baselines, and generally poor quantification.

Ideally, the reversal of flow occurs at such a speed that there is no detectable disturbance in the flow rates and pressures during the flow switching operation. A valve module 106 capable of 100 millisecond actuation times employed in an application where a sample throughput of one sample per second is being performed means that the flow to the analyzer 116 will be physically blocked for 200 milliseconds per second, or 20% of the overall sample analysis time. In various embodiments of the invention, a valve module 106 utilizing, without limitation, pneumatic valves capable of actuation speeds faster than 100 milliseconds, and preferably on the order of 30 milliseconds or less are utilized.

Pneumatic valve actuators are available from VICI Valco Instruments of Houston, Tex. Pneumatic valve actuators can be coupled to any valve (including valves from manufacturers other than VICO Valco Instruments) through a shaft coupling. Suitable valves include valves having porcelain rotors and/or diamond-like coatings, such as NANOPEAK™ valves available from Scivex, Inc. of Oak Harbor, Wis.

An additional advantage of the above-described embodiments over conventional systems is that the fluidic circuit is arranged such that the same solvent is always delivered to the mass spectrometer. Even when doing a step elution, the elution solvent is the only solution that is sprayed in to the mass spectrometer. While the wash solution containing the mass spectrometer incompatible components of the reaction mixture is diverted to waste, elution solvent is sprayed in to the mass spectrometer inlet. In this manner a stable API spray is always maintained and variation in baseline due to different background signals from wash and elution solutions is eliminated. Some advanced conventional systems divert the wash solution away from the MS inlet to avoid a buildup of non-volatile compounds in the source region. However, it can take several seconds to reestablish a stable spray in the MS inlet when the elution solvent is diverted to the MS. If the sample signal overlaps with this region of unstable spray, it can lead to problems with peak symmetry, baseline stability, and poor quantification.

Software

Software used to analyze the data generated by the analyzer 116, which may be executed by the controller 125 or another processor, enables many features of a high throughput analysis. For example, the mass spectrometer output at the end of a long analysis at high throughput consists of a series of data point in which time versus intensity values are recorded at each mass channel being analyzed. If plotted in a Cartesian coordinate system, these graphs result in a chromatogram made up of a series of peaks, wherein an integration of the area under each peak can be correlated to the concentration of the sample that was analyzed.

This integration event can be coupled to the switching of various valves in the fluidic circuit 104, in accordance with one embodiment of the invention. The time that a valve was actuated to back-elute the sample from the chromatography matrix into the mass spectrometer (or other analyzer) can be precisely recorded. It is known that until this event takes place no analyte(s) can be delivered to the mass spectrometer. Upon actuation of the valve, the mass spectrometer signal from the analyte(s) being back eluted from the chromatography matrix can be observed. The valve actuation time and the beginning of a mass spectrometer peak can be accurately mapped to one another in time, such that the peak integration algorithm consists of an integration of the mass spectrometer signal for a selected time period after each valve actuation. Even those samples that contain no detectable analyte(s) can be accurately analyzed in this manner since an identical signal window is monitored and integrated in each and every case.

In some cases, an error in the fluidic circuit 104 may lead to no signal being seen in the mass spectrometer. An example of such an error could be a fluidic reservoir in which no sample was present. This would lead to air being injected on to the column 225 rather than an aliquot of sample. In such a case, only baseline signal would be detected for all analytes. Since the final quantification relies on a relative measurement (i.e. substrate versus product or analyte versus an internal standard) such an error can be easily detected. If the sum of the two or more analyte signals is below a certain threshold, that sample can be flagged as an error.

Multiplexing

In various embodiments of the invention, the time required for rapid chromatography and inter-sample washing is much larger than the sample peak width (at half-height) at the output of the matrix. In such embodiments, there may be several seconds of baseline mass spectrometer (or other analyzer) signal before the next sample to be analyzed is delivered to the mass spectrometer. This period is effectively a loss in productivity, since the mass spectrometer is not actively quantifying samples.

Figure 3:
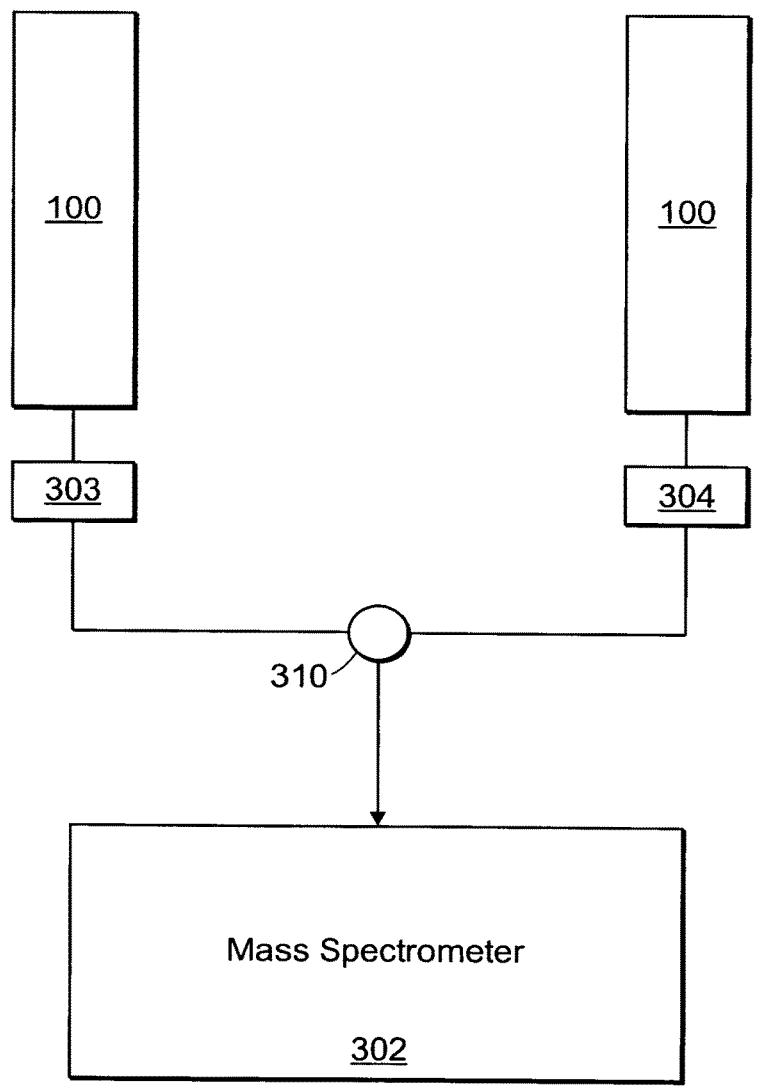
FIG. 3 is a schematic of a multiplexed analyzer system, in accordance with an embodiment of the invention.

Because mass spectrometers are large footprint instruments that require a significant capital expense, two or more high throughput mass spectrometry interfaces 303 and 304 are used to feed samples to a single mass spectrometer 302, as shown in FIG. 3 in accordance with one embodiment of the invention. Each mass spectrometry interface 303 and 304 may include, without limitation, a rapid chromatograph system 100 described above. A selection valve 310 is placed between the plurality of high throughput mass spectrometry interfaces 303 and 304 and the mass spectrometer 302. When a sample from a given high throughput mass spectrometry interface 303 or 304 is ready to be analyzed, the selection valve 310 is used to direct that sample to the mass spectrometer 302 while the remaining interfaces 303 or 304 are diverted to waste. By staggering the sample delivery to the mass spectrometer 302 such that while one interface is being actively analyzed the others are in the washing or sample acquisition steps, a plurality of interfaces 303 and 304 can be used on a single mass spectrometer 302, allowing throughput to be maximized.

Auto-Injection Device

Figure 4:
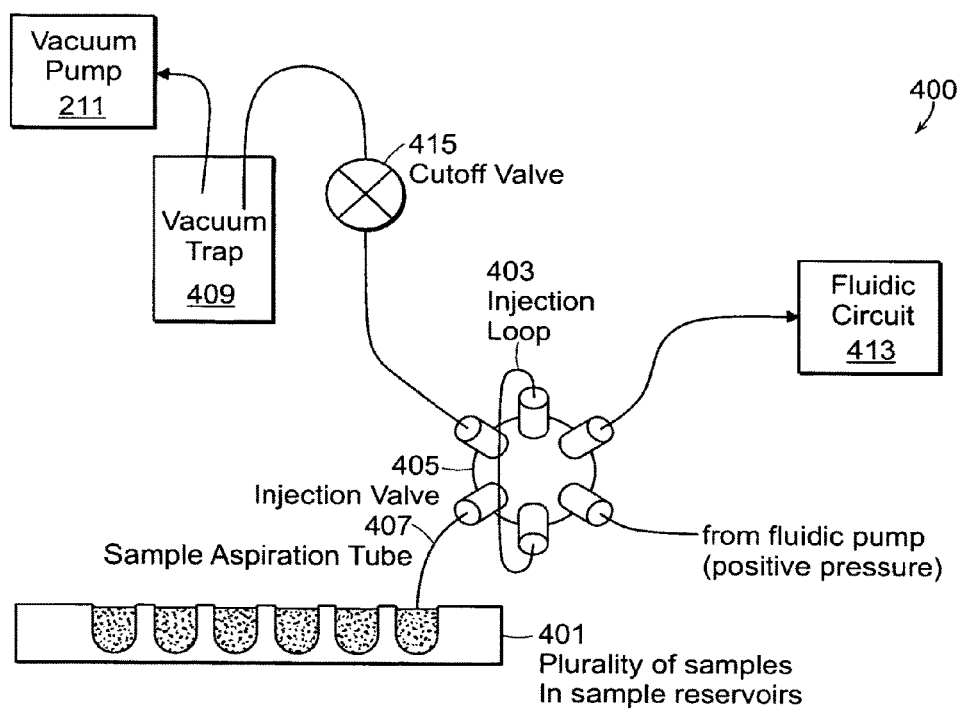
FIG. 4 is a schematic of an auto-injection device, in accordance with an embodiment of the invention.

FIG. 4 is a schematic of an auto-injection device 400 that includes a single injection valve 405, in accordance with one embodiment of the invention. The auto-injection device 400 may be used in combination with additional valves as in the above-described embodiment, and may be used to transfer samples from a sample reservoir to, without limitation, a fluidic circuit that may include an analyzer and/or a chromatography column.

Figure 5A:
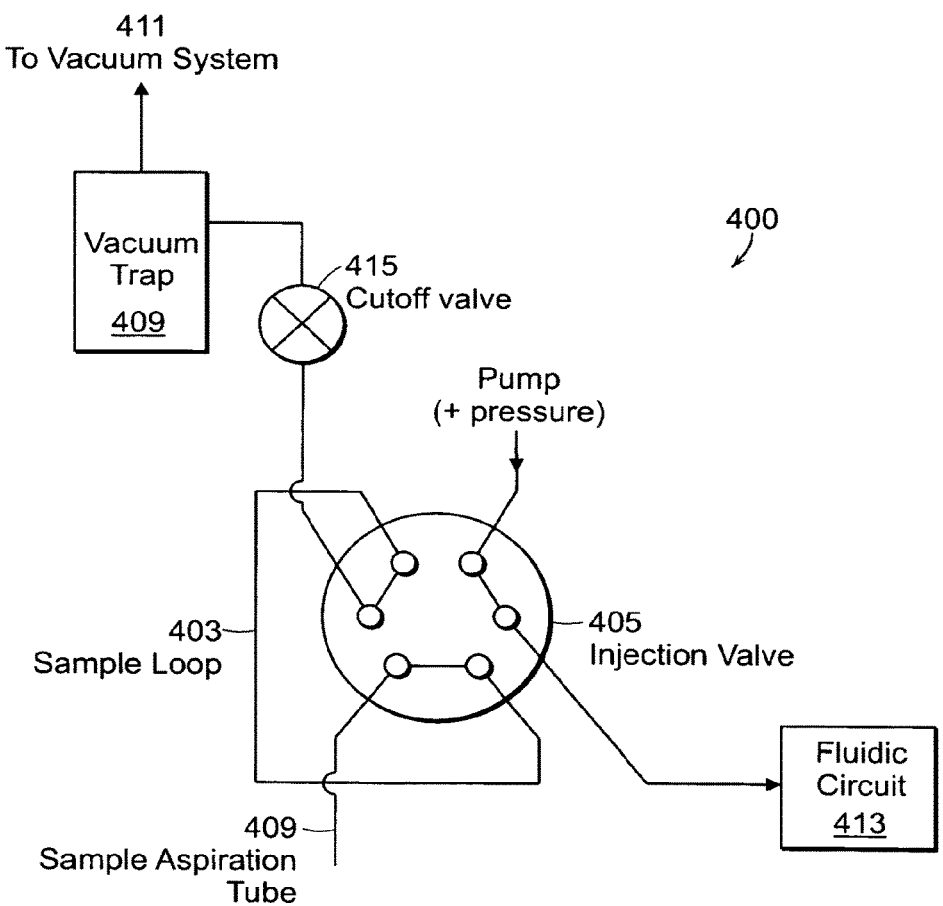
FIG. 5(a) is a schematic of the auto-injection device of FIG. 4 during sample aspiration, in accordance with an embodiment of the invention.
Figure 5B:
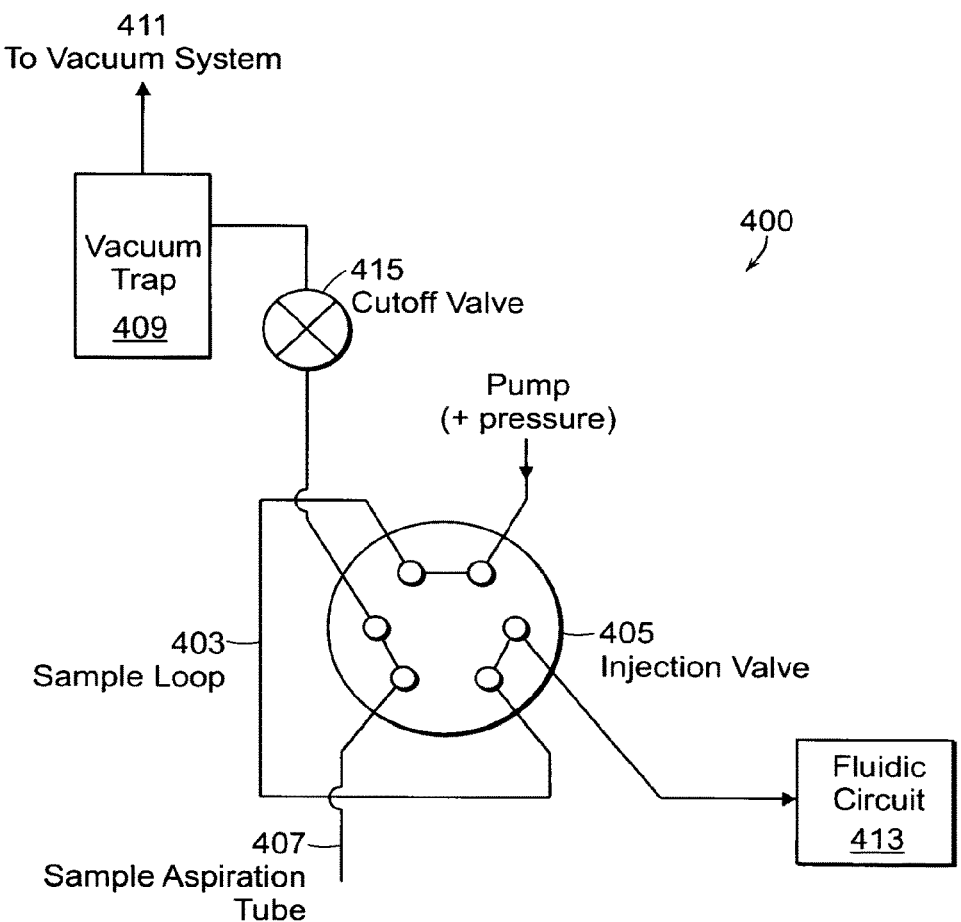
FIG. 5(b) is a schematic of the auto-injection device of FIG. 4 when aspirated sample is output to a fluidic circuit, in accordance with an embodiment of the invention.

As shown in more detail in FIG. 5(a), and similar to valve 206 in FIGS. 2(a-b), when the injection valve 405 is in a first position, (e.g. not activated), a source of reduced pressure 411 is used to aspirate a sample 401 through sample sipper tube 407 and into a sample loop 403. Upon actuation of the injection valve 405, the sample is introduced to a fluidic circuit 413 by applying increased pressure, as shown in FIG. 5(b). To clean the sipper tube 407 prior to deactivation of valve 405 and aspiration of the next sample, the aspirator tube 405 may be dipped into a wash solvent or buffer solution, with reduced pressure applied to aspirate wash solvent through the aspirator tube 104 and into trap 109. Thus, the combination of the constant negative pressure and the in-line trap eliminates the need for repetitive aspiration and dispensing of wash solution through a syringe.

Where an excess of sample is available, the reduced pressure source 411 may be, without limitation, a vacuum pump that is capable of applying a continuous vacuum to the distal end of the sample sipper tube 407. When a large enough volume of sample 401 has been aspirated into the sample loop 403 to fill it completely, the injection valve 405 is actuated and the sample is output to the fluidic circuit 413. The trap 409, located between the injection valve 405 and the vacuum pump 411 is used to collect excess sample. Changing the injection volume can be accomplished by changing the length of the sample loop 403.

However, in cases where an excess of sample 401 is not available or the sample is too valuable to expend, a metered amount of sample 401 may be aspirated into the injection valve 405. In a preferred embodiment of the injection, this metering is performed through the use of a cut-off valve 415 located between the vacuum pump 411 and the injection valve 405. In preferred embodiments, the cutoff valve 415 is a solenoid valve with very rapid response times allowing for accurate and precise actuation in the millisecond time scale. The cutoff valve 415 may be used to aspirate an aliquot of sample into the sample loop 403 through the sipper tube 407 for a very precise and controlled amount of time. The volume of sample aspirated into the sample loop 403 can be precisely calibrated based on the diameters of the sample loop 403, sample sipper tube 407, and the timing of the cutoff valve 415. The longer the cutoff valve 415 is kept in the open position, the longer the aspiration of the sample and the larger the volume of sample aspirated into the injection valve 405.

In accordance with another embodiment of the invention, the continuous vacuum system may be replaced with a piston device in fluid communication with the injection valve 403, particularly in cases where a cutoff valve 415 is impractical, or where the plurality of samples to be analyzed has large differences in viscosity. Changes in viscosity may cause changes in the rate of sample aspiration. The amount of sample aspirated into the sample loop 403 can be metered, for example, by controlling the distance the piston is withdrawn within a cylinder. A sufficient time is allocated to the aspiration process to permit the entire metered amount of sample to be loaded into the sample loop 403. Imprecision in injection volumes due to differences in rates of aspiration caused by sample viscosity can thus be eliminated. The sample is aspirated directly into the sample loop 403 and then injected into the fluidic system. There is no need to apply positive pressure from the piston until it has reached the end of its traverse within the cylinder.

In other embodiments of the invention, various combinations of the above-described approaches for aspirating sample into the injection loop through the sipper tube may be used. For example, a selection valve may be used to select whether a cutoff valve in combination with a continuous vacuum source, or alternatively, a piston device, is placed in fluid communication with the injection valve. Where an excess of sample is available, the selection valve is operated so as to place the cutoff valve and continuous vacuum in fluid communication with the injection valve, with the cutoff valve left in the open position. If the aspiration of the sample must be metered either the cutoff valve can be activated as described above, or the selection valve can be actuated to use the piston-based aspiration system.

The auto-injection device 400 is advantageous over conventional auto-injectors for several reasons. By directly aspirating the sample into the injection loop rather than into a transfer syringe, the computer controlled robotic motion required for each injection is reduced. In conventional auto-injector systems, the transfer syringe must first be moved into the sample reservoir to aspirate an aliquot of sample. Next the transfer syringe must be moved to the injection valve and the aliquot of sample loaded into the injection loop. After the injection, the syringe must be moved yet another time to one or more cleaning stations. Because the current invention aspirates the sample directly into the injection loop, the need to move the transfer syringe from the sample reservoir to the injection valve is eliminated. Minimizing robotic movement within the device both increases the throughput and the reliability of the system. By repeatedly aspirating and injecting from the same sample, larger sample volumes may be analyzed without undue delay. If the injection is to a chromatographic resin, multiple aliquots of sample may be added to the column prior to additional steps of washing and eluting.

Another advantage of the current invention is realized in the cleaning of the auto-injector between samples. All surfaces that come into contact with sample generally must be thoroughly cleaned before the next sample can be injected. In conventional auto-injectors, this includes the injection valve as well as the transfer syringe. Cleaning of the transfer syringe can be especially challenging and time consuming, especially if a standard syringe is used.

Because most syringes are manufactured from glass and stainless steel, certain samples are particularly difficult to remove. Many lipophilic compounds tend to adhere strongly to stainless steel and can lead to sample carryover or leaching. Transfer syringes typically have tubing of various diameters and are composed of multiple materials (e.g., glass and stainless steel) that are more difficult to clean than continuous and smooth bio-inert tubing. Since the current invention aspirates samples directly into the injection valve through a sipper tube, the invention does not require the cleaning of a transfer syringe. This has the double impact of decreasing sample carryover while also increasing the throughput of the device.

Of importance to minimizing sample carryover is the choice of material used for the sipper tube. In a preferred embodiment of the invention, a concentric tube injector is used to provide the ability to pierce sealed sample reservoirs without the need to have the sample come into contact with materials such as stainless steel that are not chemically compatible with a wide range of samples, as described in U.S. Pat. No. 7,100,460.

As described above, cleanup of the device can be achieved by simply aspirating a large volume of fluid through the sipper tube 407 while the sample of interest is being diverted to the fluidic circuit for analysis, as shown in FIG. 5(*b*). The use of biocompatible materials coupled with the small surface area of the sipper tube and injection valve that needs to be cleaned allows for very efficient reduction of sample carryover while maintaining a rapid throughput.

The following are examples, without limitation, of high-throughput sampling using various configurations of the above-described embodiments.

EXAMPLE 1

Drug-Drug Interaction (DDI) Assay

Many xenobiotic compounds are metabolized in vivo by a family of enzymes known as cytochrome P450s, primarily in the liver. The metabolic activity by P450 enzyme also includes a vast majority of small molecule pharmaceuticals. Since the therapeutic activity of many pharmaceutically active compounds is highly dose-dependent it is advantageous to understand the metabolic fate of these chemicals. In many cases, high doses of certain chemicals can be toxic or have long-term deleterious effects.

Many compounds are known to affect the metabolism of certain P450 enzymes, either acting as inhibitors or activators. This is true for a range of chemicals that are currently used as therapeutics. It is critical to know from a drug-safety standpoint whether or not the metabolic profile of a pharmaceutical compound taken by an individual may be affected by other chemicals that individual may be taking. If an individual is currently taking a certain drug that inhibits the action of a specific P450 enzyme, taking a second drug that is also metabolized by the same P450 enzyme can have catastrophic consequences.

The inhibitory effect of the first drug on the P450 enzyme can lead to the second drug not being metabolized at the predicted rate and result in much higher than expected in vivo concentrations. In some cases this can be toxic or even fatal. To study the possible effects of potential new pharmaceutical compounds a series of in vitro assays known as the drug-drug interaction assays have been developed and are familiar to those skilled in the art. The assays use various preparations of P450 enzymes, either as purified recombinant proteins, or as various cellular or sub-cellular (e.g. microsomes, S9 fractions, etc.) preparations of liver tissue. The enzyme preparations are allowed to react with known substrates of the P450 enzymes, known as probes, under controlled conditions in the presence of the test compounds. If the test compound is active in the assay it will cause a shift in the expected metabolism of the probe molecule. A wide range of different probes and assays has been described in the scientific literature. These formats include both optically active probes typically used with recombinant enzyme preparations and mass spectrometric approaches that facilitate the use of subcellular liver preparations and highly selective and specific probes. While the throughput of optical assays can be very high, researchers generally prefer to perform mass spectrometry-based assays since more biologically relevant data can be obtained.

The above-described embodiments of the invention can be used to vastly improve the throughput of mass spectrometry-based drug-drug interaction assays. An assay to test the activity of test compounds against cytochrome P450-2D6 (CYP2D6) was performed in a 96-well microtiter plate. A microsomal preparation from human liver tissue was incubated in the presence of dextromethorphan, the test compound, and NADPH in a buffer containing potassium phosphate at pH 7.4 and magnesium chloride. After a 30 minute incubation, the reaction was quenched by acidifying the reaction with the addition of 10% (v/v) 0.1% formic acid. While the human liver microsomes have a variety of different enzymes, dextromethorphan is a specific substrate of CYP2D6 and is metabolized into dextrorphan. While the remaining dextromethorphan substrate and the dextrorphan product formed in the reaction can be quantified by the use of conventional liquid chromatography-mass spectrometry at throughputs that is on the order of minutes per sample, the above-described embodiments of the invention allow similar analysis to be performed on the order of 5 seconds.

In accordance with an embodiment of the invention, and referring to FIGS. 2(*a*)-(*c*), the sipper tube 204 attached to the valve 206 is moved relative to the first sample to be analyzed in the 96-well microtiter plate. The distal end of the sipper 204 is immersed into the reaction buffer and an aliquot is aspirated into a 5.0 microliter injection loop 208 through the use of a vacuum 221 applied to the distal end of the sipper tube 204. Fifty milliseconds after aspiration has begun, enough fluid has been aspirated into the valve 206 to completely fill the 5.0 microliter injection loop 208. At this time the injection valve 206 is actuated and the sample in the loop 208 is brought into fluid communication with the output from a high-pressure fluidic pump 222 that pushes the 5.0 microliter sample aliquot through the injection loop 208 and onto a chromatographic column 225 containing an insoluble matrix. The matrix consists of impermeable beads that are an average of 40 microns in diameter. The surface of each bead has been derivatized with a 4-carbon long alkane chain to create a hydrophobic environment. Porous frits constrain the insoluble matrix beads within the column 225, however, the nature of the particles allows for fluid to freely move around and between the particles without an unacceptably high increase in pressure.

The high-pressure fluidic pump 222 is used to pump water at a flow rate of 1.2 milliliters per minute. When the sample reaches the column 225 the dextrorphan and dextromethorphan analytes, being lipophilic molecules, interact with the insoluble matrix beads within the column and are adsorbed onto the column 225. Compounds in the reaction buffer that interfere with mass spectrometry, including the potassium phosphate buffer, magnesium chloride salts, NADPH and NADP, are highly hydrophilic, and accordingly, are flushed through the column into a waste container. Insoluble components in the assay buffer that may have been aspirated along with the sample are small enough to move through the space between the 40 micron beads and are also removed from the analytes.

The total internal volume of the column 225 is 4.0 microliters. To remove the interfering salts at an acceptable level it is necessary to flush the column with several volumes of water. At a flow rate of 1.2 milliliters per minute, a total of 20 microliters of water per second is pumped. Therefore in the one-second wash, a total of 5 column volumes of water were pumped over the bed of matrix to remove the mass spectrometry incompatible components.

During this entire process a second fluidic pump 223 is used to pump a solution of 80% acetonitrile in water at a flow rate of 1.0 milliliters per minute directly on to a triple quadrupole mass spectrometer 240 operating in the electrospray ionization (ESI) mode. The mass spectrometer 240 was optimized to specifically monitor the dextrorphan and dextromethorphan analytes in multiple reaction monitoring (MRM) mode. A stable ESI flow was maintained and a constant baseline from the 80% acetonitrile solution was established. Exactly 1.0 seconds after the valve 222 to push the sample from the injection loop onto the matrix, the second valve 207 was actuated. This valve 207 forces the 80% acetonitrile to enter the column 225 from the direction opposite that from which the sample was loaded. Simultaneously, the output of the first pump 222 was diverted away from the column and to waste. The second valve 207 actuation brought the column 225 into fluidic contact with the second pump 223 and the analytes adsorbed on the column 225 were eluted by the 80% acetonitrile and pushed into the ESI source of the mass spectrometer 240 where they are analyzed. The two analytes were eluted simultaneously and analyzed in the mass spectrometer based on their mass to charge ratios.

Since the elution step is done in the opposite direction of the loading step, the analytes never travel through the column 225. This is an important point, since fluid traveling over a column 225 tends to undergo turbulence that can result in mixing and linear diffusion. Minimizing the linear diffusion is very important since this leads to an increase in the volume of fluid in which the sample is presented to the mass spectrometer. Best analytical data is obtained when the sample is presented in the smallest possible elution volume in the shortest amount of time. Small elution volumes lead to high local concentrations of analyte and a correspondingly high signal level that can be distinguished from the background signal and shot noise. In 1.5 seconds at a flow rate of 1.0 milliliters per minute a total of 25 microliters of elution fluid was pushed over the column 224. This corresponds to over 6 column volumes of elution fluid, more than enough to flush the column and eliminate carryover to the next sample.

At this time both valves 222 and 207 were actuated again to their starting positions. The injection loop 208 was available to aspirate the next sample, the 80% acetonitrile from the second high pressure pump 223 was diverted away from the column 225 and directly to the mass spectrometer 240 and the water from the first high pressure pump 222 was pushed over the column 225 in the original direction. This state was maintained for a minimum of 2 column volumes to (a minimum of 400 milliseconds) to allow the local environment within the matrix of the column 225 to be flushed with water to allow binding of the analytes in the next sample. This process is known as column equilibration and must be performed in sufficient time to allow proper analysis. After the equilibration of the column 225 the next sample was ready for analysis.

While the sample was being analyzed 80% acetonitrile from a reservoir was aspirated through the sipper tube 204 to remove any contamination in the sipper tube and to eliminate carryover into the next sample. In this manner, samples were analyzed at a periodic rate of 5 seconds per sample. It is also possible to analyze more than two analytes simultaneously and therefore to multiplex assays for multiple P450 isoforms.

EXAMPLE 2

Metabolic Stability Assay

In accordance with various embodiments of the invention, certain attributes of the system may be advantageously enhanced at the expense of throughput. An example of such an application is the metabolic stability assay. The metabolic stability assay assesses the activity of liver enzymes on a test molecule. It is typically an in vitro assay performed by incubating a sub-cellular liver preparation (e.g. liver microsomes or S9 fraction) with a source of energy (e.g. NADPH) and the test compound in an appropriate buffer system. The liver enzymes may metabolize the test compound, the rate of which can be determined by quantifying the amount of the test compound at controlled times using mass spectrometry.

This assay is different from the DDI assay in that each and every test compound must be monitored in the mass spectrometer. In the DDI assay, only a specific set of probes needed to be monitored allowing for a full optimization of the system. Given that a very wide range of test compounds needs to be analyzed in the metabolic stability assay, generic methods capable of analyzing many different chemical structures are required. In this application, the throughput of the system is lowered slightly to facilitate the analysis of a wider range of analytes.

To perform the metabolic stability assay, a different approach than the DDI assay is used. The reverse elution (i.e., eluting the analytes from the column in the opposite direction to which it was loaded onto the column) is not used. Rather, the analytes are eluted from the column in the same direction as they were loaded on to the column. This results in linear diffusion as the analytes experience turbulent flow as they are pushed over the insoluble matrix beads, causing a broader peak and therefore lower throughput. However, many of the aspects of the invention used in the DDI assay can still be applied to the assay and result in a significantly increased throughput over conventional methods without a sacrifice in the sensitivity of the assay. These advantages will be described in detail below.

The sample aliquot is aspirated into an injection loop and loaded onto the column in the same manner as in the DDI assay with a first high-pressure pump that is used to pump a wash solution. This solution is typically water or an aqueous buffer and is used to flush out the salts, buffer components, NADPH, and insoluble components of the reaction mixture to a waste container. During this time a second high pressure pump is used to pump an elution solvent in to the ESI or APCI source of the mass spectrometer. When the second valve is actuated, the elution fluid is forced over the column in the same direction that the analytes were loaded on to the column. An elution fluid that is capable of dissolving a very wide range of chemicals but is compatible with atmospheric pressure ionization mass spectrometry is used. These buffers may include alcohols (e.g. methanol, ethanol, or isopropanol), acetonitrile, acetone, tetrahydrofuran or mixtures of these solvents. It is generally desirable to have a small amount of water in the mixture, and additives such as ammonium acetate, ammonium carbonate, or DMSO to the elution solution may result in sharper peaks.

If the mass spectrometric characteristics of the analytes of interest are previously known, the mass spectrometer can be set up to specifically monitor those compounds in MRM mode. However, if no previous information is available about the analytes, it may be desirable to use a mass spectrometer to scan a range of masses. The use of a time-of-flight, ion trap, hybrid quadrupole/ion trap, or hybrid quadrupole/time-of-flight mass spectrometer can facilitate the scanning of a wide range of masses with minimal loss in signal intensity. To obtain good quantitative data an internal standard is added upon the quenching of the reaction and the signal from the analyte(s) is normalized with respect to the internal standard.

The current invention uses a step-elution system to purify samples using column chromatography and analyses them using mass spectrometry. However, the system uses a significant improvement over conventional step elution systems: the same solvent system (the elution solution) is always sprayed into the inlet of the mass spectrometer. In conventional systems, as the wash and elution solutions are alternated for each sample and the two different solutions are alternately sprayed in to the mass spectrometer inlet. This can have a huge impact on the baseline signal observed. The variation is baseline signal may have a significant impact on the quantification of peaks, particularly those that have a low level of signal.

In some of the more advanced conventional systems the wash solution is diverted away from the mass spectrometer inlet to a waste container and only the elution solution is sprayed into the mass spectrometer. However, this also results in a change in the background signal seen in the mass spectrometer since there is no flow during the column loading and washing stages. Furthermore it may take several seconds to reestablish a stable spray in the MS inlet. In a high throughput system such as described here, the leading edge of the analyte peak may overlap with the region of unstable flow resulting in poor sensitivity, uneven peak shape and increased error in quantification.

A further improvement the current invention provides over conventional systems is in the fast switching valves. Typical electronically actuated valves provide switching times over 100 milliseconds. However the very fast valve switching (e.g. 50 milliseconds or less) employed in the current invention allows for a pulse-free spray in the mass spectrometer providing symmetrical peaks with flat baselines and facilitates accurate quantification.

EXAMPLE 3

Compound Purity Testing

In some applications, the samples to be analyzed are already in a buffer that is compatible with mass spectrometry. Such an application may be the quality control analysis of test compounds in an aqueous or organic buffer that can directly be sprayed in to an API source without the need for any purification. Various aspects of the above-described embodiments can be used to increase the sample throughput for such an application.

In this application only a single injection valve is used. An aliquot of sample is aspirated into the injection loop and upon actuation of that valve the sample is sprayed directly in to the mass spectrometer. The flow from a single fluidic pump is used to push the sample through the injection loop and into the inlet of the mass spectrometer. In preferred embodiments of the invention, the fluid used to push the sample on to the mass spectrometer is one that the analytes are highly soluble in and provides good ionization in the mass spectrometer inlet. These solutions may include alcohols (e.g. methanol, ethanol, or isopropanol), acetonitrile, acetone, tetrahydrofuran or mixtures of one or more of these solvents with water.

The system provides increased throughput over conventional systems through several means. The elimination of a transport syringe to move a sample aliquot from a reservoir to the injection valve increases the overall speed of the robotics. The injection valve and the sample reservoir may be moved relative to each other such that an aliquot of sample can be directly aspirated in to the injection loop. Besides facilitating faster robotics, this also eliminates the need to clean the transport syringe between injections. In conventional systems both the transport syringe and the injection loop need to be thoroughly cleaned between samples. However, in the current invention there is no transport syringe.

Samples that do not need to be purified have been analyzed by atmospheric pressure ionization at throughputs of approximately 1 second per sample using the system with minimal carryover between samples.

Avoiding Sample-To-Sample Carryover

As explained above, the entire fluidic system is properly cleaned between analyses to ensure that carryover from a given sample does not confound the analysis of the next sample in the cue. Cleaning of the fluidic system is achieved by flushing the fluidic system with a solvent that the confounding compounds are freely soluble in. The fluidic system described herein is composed of two major components, each associated with a valve assembly. A first valve contains an injection loop and a sample aspiration tube through which an aliquot of a fluidic sample to be analyzed is aspirated into the injection loop. This valve arrangement is in fluid communication with the second valve that contains a chromatography system containing an insoluble matrix that is capable of purifying the sample prior to analysis.

Samples aspirated into the injection loop are loaded onto the chromatography column and washed with a "wash solution" in a first direction and, after an appropriate purification has been performed, the samples are eluted from the chromatography column with an elution solution in a second direction, opposite to the first direction. Since the elution solution removes the sample from the column by solubilizing it, it has the secondary effect of cleaning the chromatography column and effectively reducing carryover into the next sample. Several column volumes of elution solution may be necessary to reduce carryover to an acceptable level, depending on the exact nature of the analyte of interest and elution solvent used. A larger volume of elution solvent can be delivered to the column by increasing the time that the column is flushed with the elution solution in the second direction.

While the action of eluting the analyte off of the chromatography system has the added benefit of cleaning the column and valve assembly, carryover can also result from traces of analyte left in the injection loop, sample aspiration tube, or in the portions of initial valve. This portion of the fluidic circuit can also be flushed with elution solution to clean the system between samples and eliminate or minimize carryover effects. In one embodiment of the invention, the sample aspiration tube can be moved to a reservoir containing elution solvent. The valve can be actuated such that the sample loop is in fluid communication with the sample aspiration tube, and a necessary volume of elution buffer can be aspirated through the sample aspiration tube and the injection loop. The solvent so aspirated will be collected in the in-line trap downstream of the valve before the source of vacuum.

In one representative embodiment, the aspiration of the elution solvent through the sample aspiration tube and injection loop will occur simultaneously with the back elution of the analyte from the chromatography column to the analyzer. This allows maximizing of the throughput since the flushing of the first valve containing the sample injection loop will be achieved during the time that the sample is being eluted. However, there may be particularly difficult analytes (e.g. very hydrophobic compounds) that despite the use of bioinert materials and surface coatings still cause carryover to be observed. These particularly difficult analytes may require a large volume elution solvent to be aspirated through the sample aspiration tube and the injection loop to eliminate carryover to an acceptable level. In some cases the aspiration of a large volume of elution solution through the sample aspiration tube and the injection loop may take longer than the back-elution of the analytes from the chromatography column to the analyzer. In such a case flushing the fluidic circuit to minimize carryover becomes a limiting factor for system throughput.

Thus another embodiment of the invention addresses the case of those analytes where flushing the fluidic system is a throughput-limiting event. Such an embodiment increases the volume of elution solvent with which a portion of the fluidic system is flushed between samples to further minimize carryover while still maximizing sample throughput. To this end, an additional fluidic valve can be used. This valve can be a selection valve or a 4-port injection valve. In one embodiment, a 6-port injection valve is used which is identical to the two existing valves where 2 of the ports have been short-circuited with a piece of tubing. The use of identical valves throughout the fluidic circuit has advantages in manufacturing, inventory management, and servicing of the instrument.

The fluidic valve associated with the sample injection loop (valve 1) is flushed with elution fluid from a positive pressure source, such as an additional high-pressure fluidic pump, rather than being aspirated through the valve with a vacuum as described above. The use of positive pressure allows for a much larger volume of fluid to be flushed through the valve in a given amount of time as compared to the use of vacuum aspiration. Under normal conditions, the maximum pressure with which a fluid can be aspirated is 1 atmosphere, assuming a perfect vacuum can be applied. In comparison, a standard high-pressure pump can apply tens of atmospheres of fluidic pressure, resulting in a much larger volume of fluid being delivered in an equivalent amount of time.

In this embodiment, the sample is aspirated into the sample loop on valve 1 as before. The valve is then actuated and the analytes are diverted to the second valve and loaded onto the chromatography column as before. Once the sample is purified through flushing with an appropriate volume of wash solution, valve 2 is actuated and the sample is back-eluted onto the analyzer with elution solution. During this time the additional upstream valve is simultaneously actuated to flush the fluidic circuit in valve 1 (including the sample injection loop) with elution solution. The sample aspiration tube is not in fluid communication with the sample loop at this time, and still must be flushed with aspiration of elution solution from an appropriate reservoir. Before the next sample is aspirated the additional valve is actuated once again and wash solution is flushed through the fluidic system and the chromatography column to equilibrate the system.

Three-Valve Embodiment

Figure 6A:
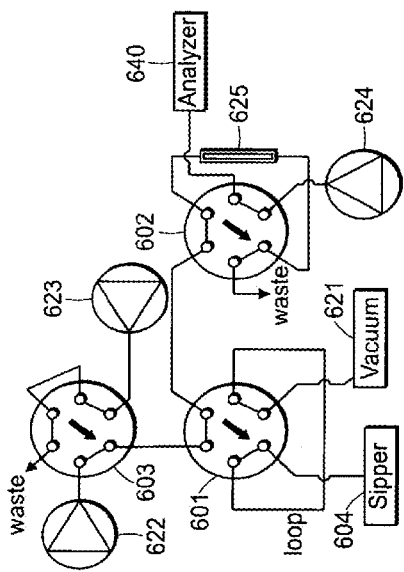
FIGS. 6(a)-6(d) is a schematic of an embodiment using three valves.

FIGS. 6(A)-(D) show an embodiment of the present invention using a three-valve and three-pump arrangement as described above. FIG. 6(A) shows the first assay phase in which a liquid sample is loaded into the sample injection loop. A sipper tube 604 is lowered into the sample reservoir and an aliquot of sample is aspirated into the injection loop via sample injection valve 601 much as described before with respect to two-valve embodiments. Any excess sample aspirated is collected in a vacuum trap 621 downstream of the loop. During this time fresh elution solvent is delivered to the analyzer 640 from first elution solvent pump 624 to establish and maintain stable ESI or APCI spray and a corresponding stable baseline signal from the mass spectrometer. The column 625 is equilibrated by pumping wash buffer (typically an aqueous solution) from wash solvent pump 622. Second elution solvent pump 623 is diverted directly to waste by solvent valve 603.

Figure 6B:
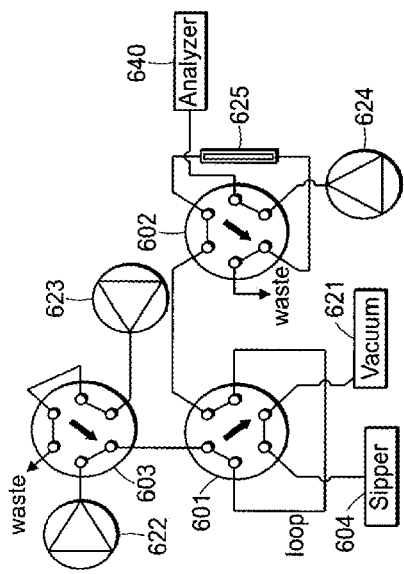

FIG. 6(B) shows the next phase, in which the valves are aligned to load the sample onto the column 625 and wash the lines. Sample injection valve 601 is actuated and the sipper tube 604 is raised out of the sample reservoir. The sample aspirated into the injection loop is delivered to the column 625 where the analytes of interest bind, but interfering compounds (e.g., salts, detergents, etc.) pass over the column 625 and are sent to waste. An appropriate number of column volumes of wash buffer are pumped to over the column 625 to ensure that the sample is purified properly.

Figure 6C:
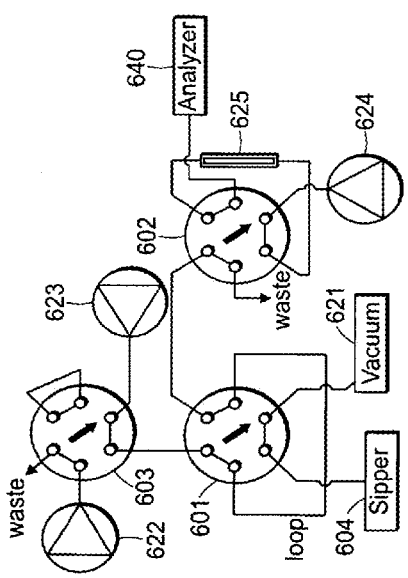

Next, as shown in FIG. 6(C), the sample is back eluted off the column 625 into the analyzer 640. Column control valve 602 and wash control valve 603 are simultaneously actuated while the sipper tube 604 is moved into the "wash solution" reservoir. The wash solution is aspirated through the sipper tube 604 to clean it and eliminate sample-to-sample carryover. Actuation of column control valve 602 results in the elution solvent from first elution pump 624 to be delivered to the column 625 in the opposite direction and the bound sample is back-eluted into the analyzer 640. An appropriate number of column volumes are pumped over the column 625 to fully elute the sample. Actuation of wash control valve 603 causes elution solvent to be pumped by second elution pump 623 over the injection loop and diverted to waste. This allows for a complete flushing of the injection loop with elution solvent between each sample and helps to minimize carryover.

Figure 6D:
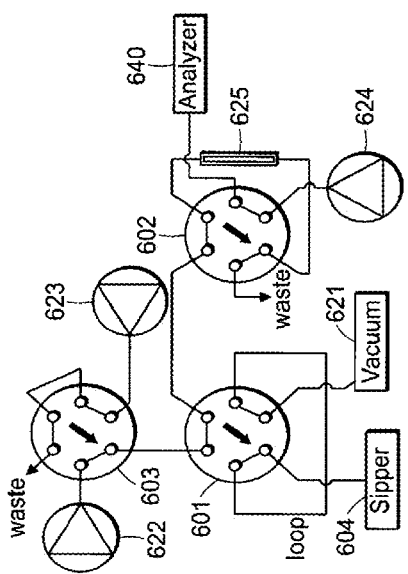

Finally, FIG. 6(D) shows equilibration of the column 625 and aspiration of the next sample. All three valves 601, 602 and 603 are simultaneously actuated to their home positions. Fresh elution solvent is pumped to the analyzer 640 from first elution solvent pump 624, while wash solvent is pumped over the column 625 in the forward direction. An appropriate number of column volumes are pumped over the column 625 to ensure column equilibration. The sipper tube 604 is then dipped into the next sample, an aliquot is aspirated into the injection loop, and the cycle is repeated.

The term "column volume" is referred to several times. A variety of column geometries, volumes, and packing can be used in various specific applications and may be optimized for each application. Both physical characteristics of the packing material (i.e., particle size, shape, porosity, etc.) and packing chemistry (i.e., C-18 vs. polymeric packings, etc.) are important in optimizing a give embodiment. Typically, column bed volumes under 10 μL are used. At a flow rate of 1.2 mL/min, 20 μL/second is delivered to the column 625. This means that in a typical 1.5 second elution, 3 volumes of a 10 μL column or 6 volumes of a 5 μL column can be realized. Maximum throughput is achieved by using the smallest acceptable column bed volume for a given application.

The elution solvent (usually an organic solvent) is delivered to the analyzer 640 in an uninterrupted manner at a constant flow rate. Even though a step elution is performed, only the elution solvent is delivered to the analyzer 640 in this arrangement. This allows for a stable ESI or APCI flow to be established and a constant baseline to be achieved. Analytes are simply "inserted" into this flow with the actuation of column control valve 602 facilitating very sharp and symmetrical peaks on a constant and stable baseline.

Other methods for performing a fast-step elution may be somewhat problematic. For example, the wash solution and elution solvent can be delivered to the analyzer 640 in a periodic manner. But this can result in large changes in background signal from the two solutions. Attempting to deconvolute a peak on a changing baseline is very troublesome. Also, the wash solution (typically containing the salts and other incompatible components of the sample mixture) can be diverted to waste and only the elution solution diverted to the analyzer 640. But establishing a stable ESI flow can take significant time and if the analytes of interest are delivered to the analyzer 640 before a stable flow is established, sensitivity and quantification issues are encountered.

Standard electro-mechanically activated valves may not be appropriate in the embodiments just described due to slow actuation times. Since the valves do not permit fluid communication during the actuation process, flow is physically cut. The interruption in flow manifests itself as a "negative" peak in the baseline signal twice per cycle (actuation the valve and then returning to the home position). Given the throughputs of specific embodiments, at least one of these two "negative" peaks interferes with the analyte signal from the analyzer 640 resulting in a double peak that impacts on quantification and data quality. The solution is a very fast actuating valve (e.g., 30 μsec actuation time or faster) which has been engineered specifically for the task. The actuation time of the valves should be rapid enough that no interruption to the flow can be observed physically or in the data.

Wash control valve 603 can be replaced with a 4-port valve. However, to keep manufacturing and parts inventory simple, a six-port valve identical to valves 601 and 602 may be preferred, and 2 ports can be permanently "short-circuited" with a piece of tubing. To reduce sample carryover and promote valve performance and durability, various valve components (e.g. the stator) can be formed from ceramics and can be coated with materials such as polytetrafluoroethylene (PTFE) or diamond-like carbon (DLC). Suitable valves include part number S-15287 available from Upchurch Scientific, Inc. of Oak Harbor, Wash.

Wash control valve 603 also could be eliminated from the system and the injection loop could be cleaned between samples by placing the sipper tube 604 into the wash solution and aspirating solvent through the sample supply valve 601 in the "load" position where the injection loop is in fluid communication with the sipper tube 604. However, a greater amount of fluid can be pumped with positive pressure than can be aspirated with negative pressure in a given amount of time. For analytes where sample-to-sample carryover is problematic, the use of wash control valve 603 can help minimize carryover by washing the loop with a greater amount of solvent while maintaining throughput.

The valves can be actuated by an electric or pneumatic actuation. Suitable actuators include the VEXTA® two-phase stepping motor, available from Oriental Motor Co., Ltd. of Tokyo, Japan under part number P0040-9212KE. The actuator and the valve can be coupled by part number DK/GS 9 from GERWAH Drive Components, LP of Fayetteville, Ga.

In certain embodiments, the valve actuator(s) is controlled with software and/or hardware. The software and/or hardware can control the timing of movement of the valve actuator(s). Additionally, the software and/or hardware can control the velocity and/or acceleration of the valves to achieve optimal performance and/or longevity. For example, in high-speed application, it is desirable to apply a braking or decelerating force as the valve approaches the desired position in order to prevent damage to the valve.

Figure 6E:
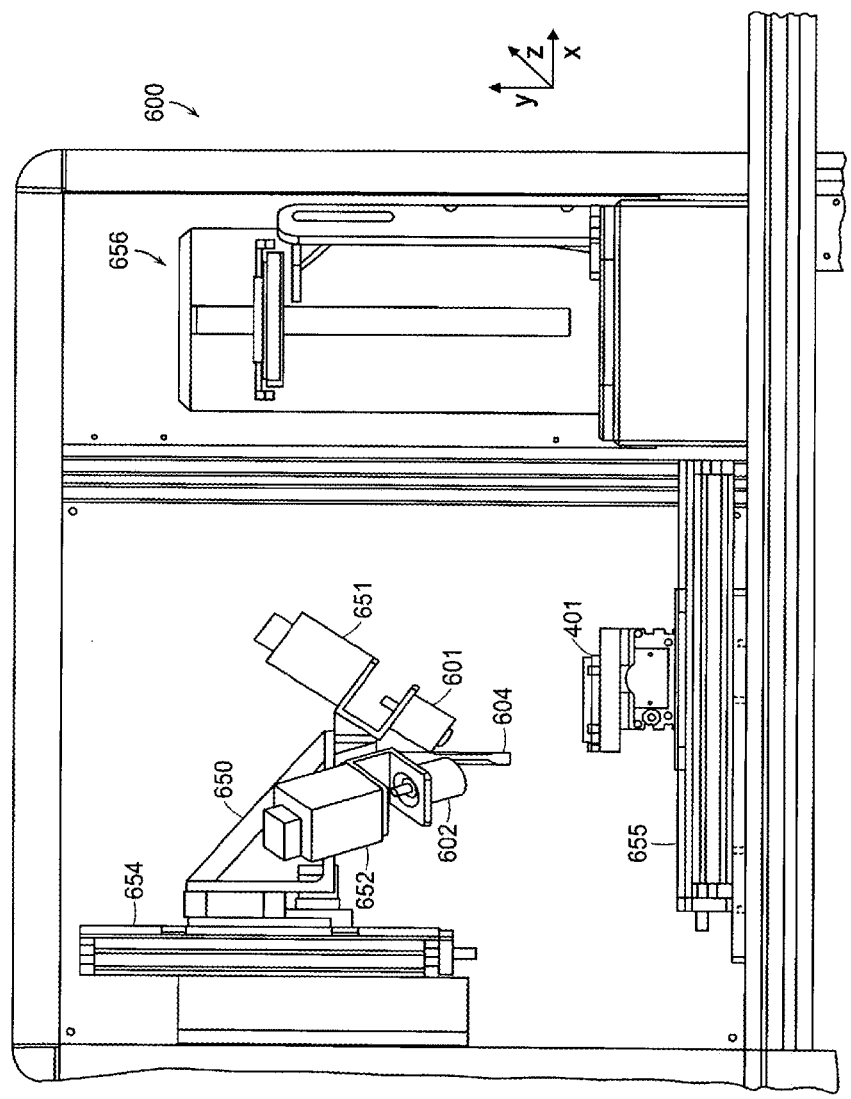
FIG. 6(e) depicts an embodiment of a three-valve auto-injective device.

FIG. 6(E) depicts an embodiment of the three-valve embodiment. System 600 includes valves 601, 602, and 603 (not visible), and sipper 604, all mounted on a bracket 650. The valves 601, 602, 603 are connected by tubing as depicted in FIG. 6(a). Advantageously, by mounting the valves 601, 602, 603, and sipper 604 on the bracket, the length of tubing required is minimized, which enables higher throughput as smaller volumes are held in the tubing.

Each motor 651, 652, and 653 (not visible) is also mounted on bracket 650 for actuation of valves 601, 602, and 603. In some embodiments, the sipper 604 is a sipper in accordance with U.S. Pat. No. 7,100,460.

The bracket 650, along with the sipper 605 can be moved at least vertically (i.e. in the ydirection) by control assembly 654, which can be an electrical, mechanical, or electromechanical device as known to those of skill in the art. Likewise, reservoir plate 401 can be moved at least in the x and z directions by control assembly 655, which can be an electrical, mechanical, or electromechanical device as known to those of skill in the art. Control device 655 can interact with plate handling device 656 to obtain pre-loaded plates 401 and return plates after samples are extracted.

Figure 6F:
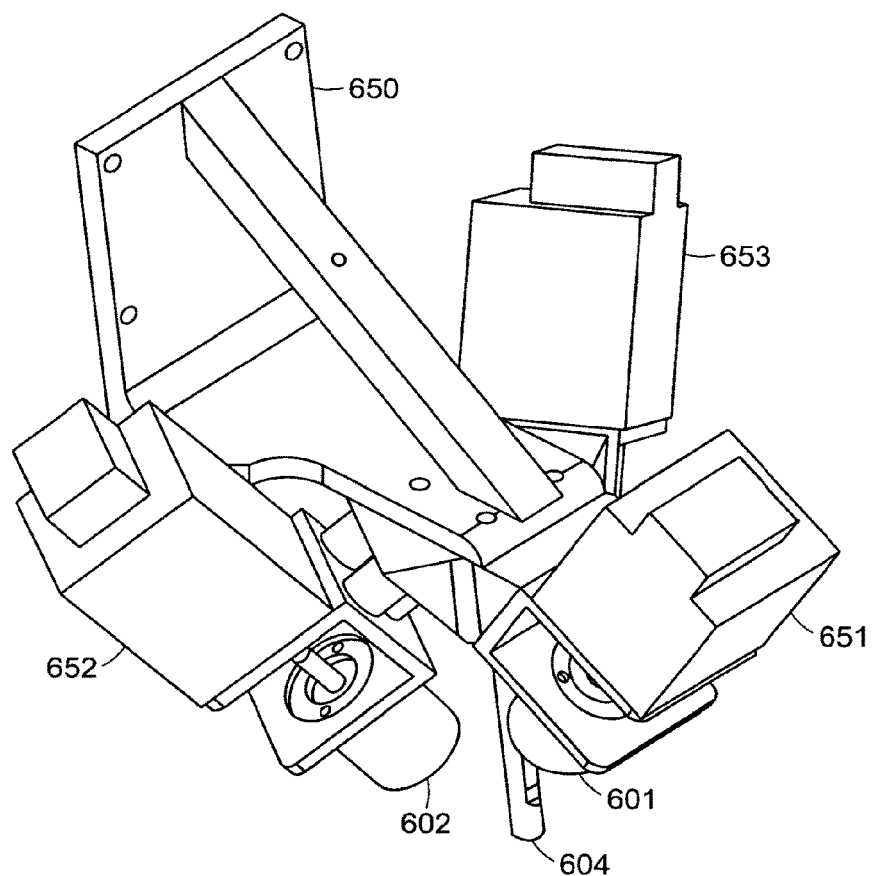
FIG. 6(f) is an isometric projection of a bracket for supporting a three-valve auto-injection device.

FIG. 6(F) provides an isometric projection of bracket 650, with valves 601, 602, 603 (again, not visible), motors 651, 652, and 653, and sipper 604. As seen more clearly in FIG. 6(E), valves 601, 602, and 603 are mounted at angles so that the tubing distance between each valve can be further reduced.

When used in conjunction with other aspects of this invention, such as the use of bio-inert materials and surface coatings, three valve embodiments result in a minimum amount of carryover for even the most difficult compounds, while allowing for a very high rate of sample analysis.

Improved Fluid Injection Valve Timing

Another embodiment of the present invention provides a device and method for the rapid sequential analysis of a plurality of samples. The device comprises a computer controlled robotic system that aspirates an aliquot of fluidic sample from a sample reservoir directly into an injection loop in a fluidic injection valve. This improvement allows for the device in the current injection to realize higher throughputs while minimizing sample carryover.

Figure 7:
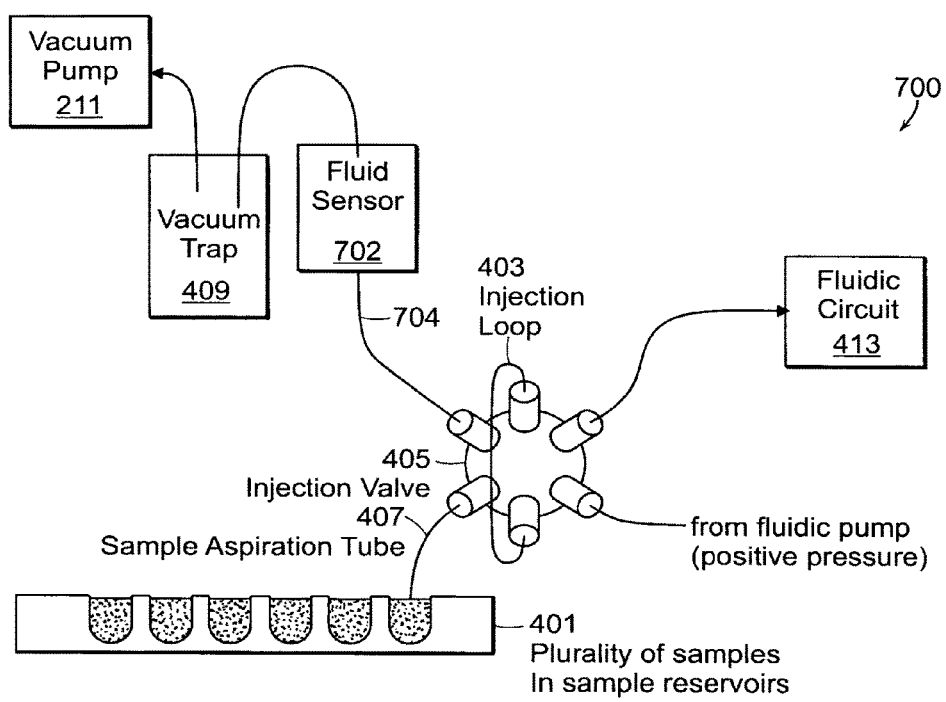
FIG. 7 is a schematic of an auto-injection device incorporating a fluid sensor, in accordance with an embodiment of the invention.

As depicted in FIG. 7, activation of the valve is controlled by a feedback mechanism that includes a fluidic sensor 702 located between injection valve 405 and vacuum trap 409. Fluid sensor 702 detects the presence of fluid in conduit 704. The fluid sensor 702 is used to control the precise timing at which the injection valve 405 is actuated as well as determining the position of the sample aspiration tube 407 with respect to the fluidic sample to be analyzed. Several embodiments of the invention are described below.

In accordance with one aspect of the invention, the transfer syringe is completely eliminated from the auto-injection device. The sample to be analyzed is aspirated directly in to the injection loop 403 of the injection valve 405 through an aspiration tube 407 attached directly to a port of the injection valve 405. The computer-controlled robotic system of the device allows for the movement of the aspiration tube 407 connected to the injection valve 405 to be moved relative to the sample reservoirs 401.

An aliquot of sample can be aspirated directly into the injection valve 405 through the aspiration tube 407 in a number of ways. In cases where an excess of sample is available and continuous vacuum may be applied to the distal end of the injection valve 405 with a vacuum pump 211. When a large enough volume of sample has been aspirated into the injection loop 403 to fill it completely the injection valve 405 is actuated and the sample is introduced to the fluidic circuit. A trap 409 located between the injection valve 405 and the vacuum pump 211 is used to collect excess sample. In this embodiment of the invention, the amount of sample injected is controlled solely through the volume of the injection loop 403. Changing the injection volume requires changing the injection loop of the device.

During sample analysis it is important that the injection volume is known such that an accurate measurement is achieved. This is particularly important when a plurality of samples is analyzed serially, since an inconsistent injection volume may lead to variability in the measurements. The current invention relates to a device and method that ensures that a full injection loop with a minimum amount of sample is achieved with every sample aspiration, even in cases where the viscosity, amount, temperature, or other physical parameters of a plurality of samples may differ.

As the aspiration tube 407 is lowered into the fluidic sample 401, the aspiration tube 407, injection loop 403, and valve 405 will be free of liquid and contain only ambient air. When the aspiration tube 407 is dipped into the fluidic sample 401, the sample 401 will be drawn into the aspiration tube 407 and fill the injection loop 403 and eventually be collected within a vacuum trap 409. Actuation of the injection valve 405 results in the volume of fluidic sample located within the injection loop 403 to be introduced into the sample purification or analysis device. The timing of this actuation is critical since actuation of the valve 405 too quickly results in an incompletely full injection loop 403 while actuation of the valve 405 too late results in a waste of sample. In cases where only a small amount of fluidic sample is available for analysis, a late valve actuation may lead to the entire sample traveling through the injection loop 403 and being collected in the vacuum trap 409, resulting in an incomplete or empty injection loop 403 and a loss of the sample.

While it is possible to determine the timing of the proper valve actuation empirically, this is a time consuming and error-prone process that typically results in an excess of sample being aspirated leading to waste. Empirical determination of the valve actuation timing becomes exceedingly difficult when the volume of the fluidic sample to be analyzed is very small. Furthermore, small changes in the physical characteristics of the fluidic sample, such as the viscosity, temperature, or insoluble materials such as cellular or subcellular components can greatly affect the sample aspiration rate leading to inconsistency when a plurality of samples is aspirated. The present invention overcomes these problems.

The present invention provides a device wherein activation of injection valve 405 is controlled by sensor 702. In some embodiments, the sensor 702 also controls certain aspects of the sample aspiration process.

In one embodiment, the device of the current invention comprises a sensor 702 that is placed between the injection loop 403 and the vacuum source 211. When fluidic sample reaches the sensor 702 the interface between air and fluid generates a signal that is used to trigger the actuation of the injection valve 405. The presence of fluid at the sensor 702 can only be achieved when the sample aspiration tube 407 and injection loop 403 are completely full of fluidic sample. By minimizing the volume between the distal end of the injection loop 403 and sensor 702 the amount of sample that is aspirated prior to the actuation of the valve 405 can be minimized, resulting in a minimal amount of sample being wasted during the analysis.

Figure 8A:
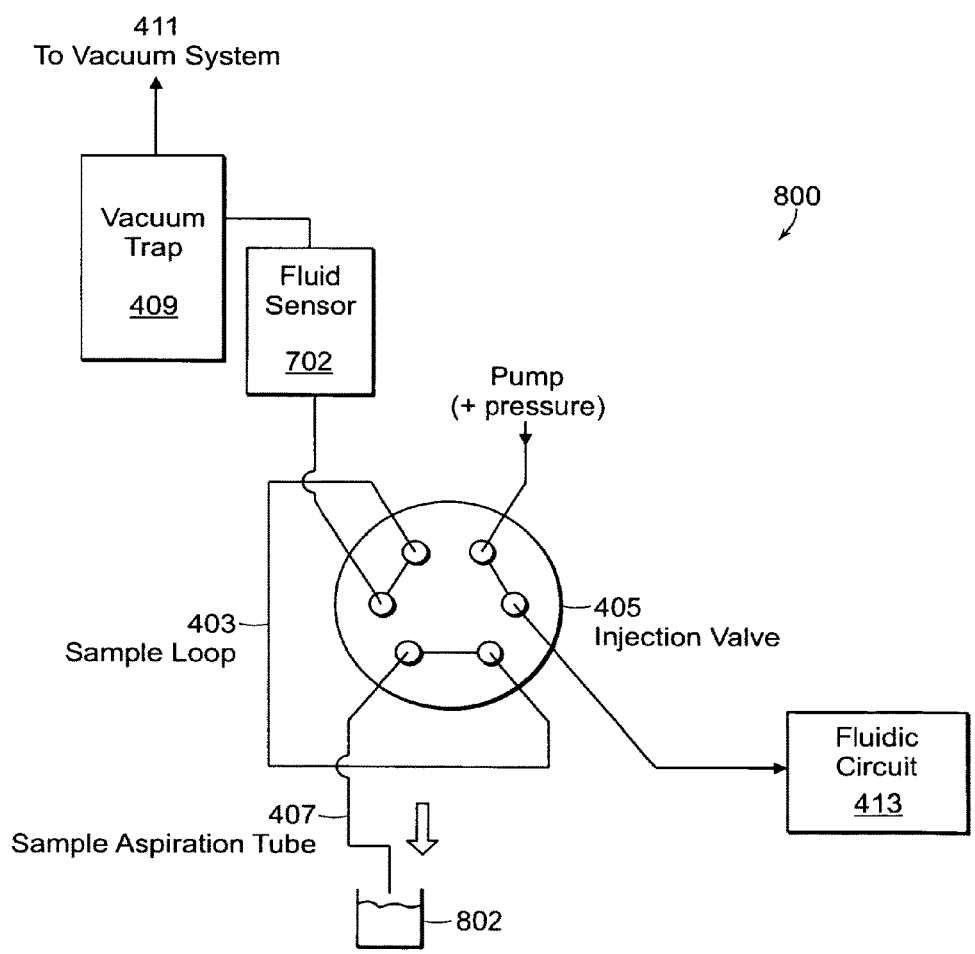
FIG. 8(a) is a schematic of the auto-injection device of FIG. 7 before sample aspiration, in accordance with an embodiment of the invention.
Figure 8B:
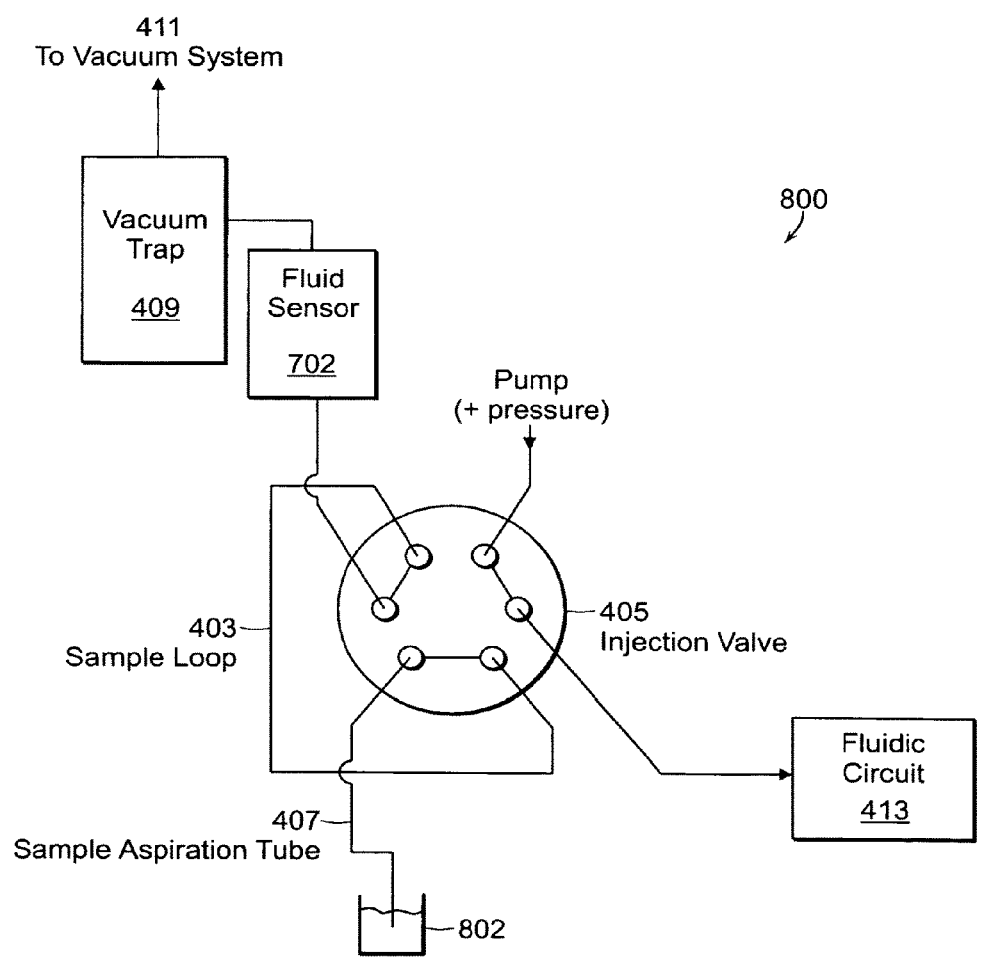
FIG. 8(b) is a schematic of the auto-injection device of FIG. 7 during sample aspiration, in accordance with an embodiment of the invention.
Figure 8C:
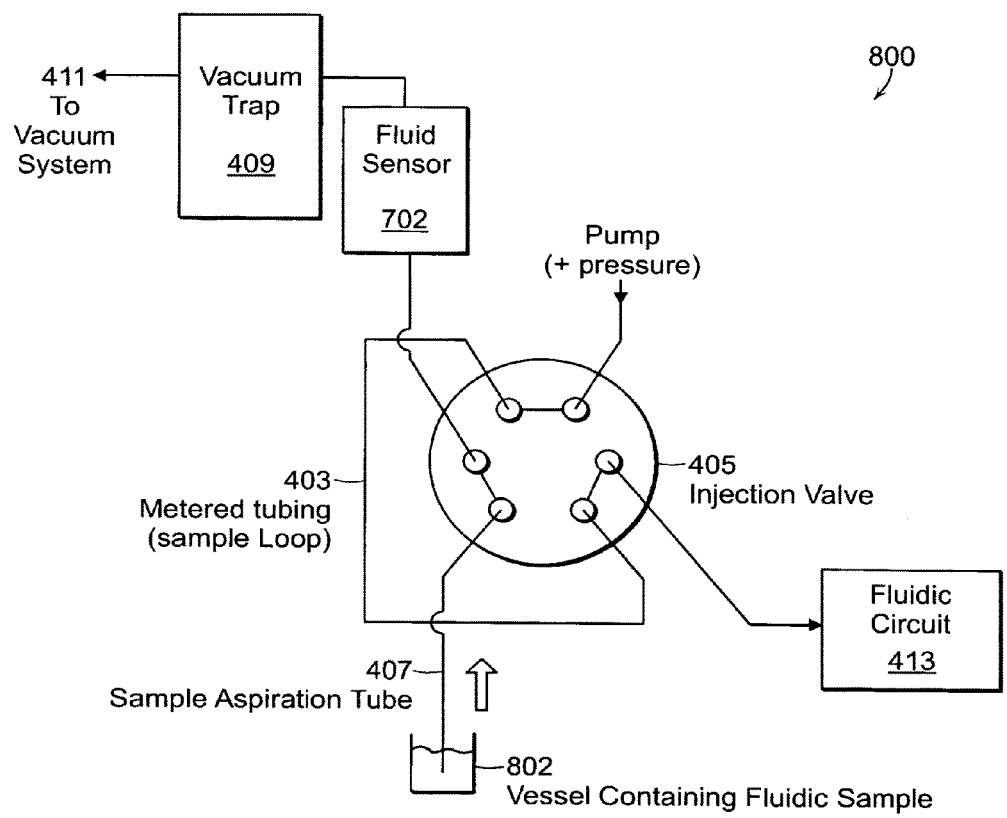
FIG. 8(c) is a schematic of the auto-injection device of FIG. 7 when aspirated sample is output to a fluidic circuit, in accordance with an embodiment of the invention.

In another preferred embodiment of the present invention, feedback from the sensor 702 is used not only to trigger the actuation of the injection valve 405 when the sample injection loop 403 is full, but also to control the mechanical movement of the sample aspiration tube 407. In this embodiment, as depicted in FIGS. 8(a)-(c), the sample aspiration tube 407 is lowered into the vessel 802 in which the fluidic sample to be analyzed is contained. The level of fluid within this vessel 802 does not need to be known a priori. When the aspiration tube 407 is moved to a position below the level of the fluidic sample (FIG. 8(b)), the sample will be aspirated through the aspiration tube 407 into the loop 403. When the loop 403 is full and the fluidic sample reaches and triggers the sensor 702, the injection valve 405 will be actuated and the sample aspiration tube 407 will be moved such that it is removed from the fluidic sample, typically by raising it up and out of the vessel 802 containing the fluidic sample (FIG. 8(c)). In this manner, vessels 802 with differing amounts of fluidic volumes can be accurately interrogated without any previous knowledge of the volume of sample in each vessel 802. Furthermore, multiple analyses be required from a single vessel 802, the movement of the sample aspiration tube will automatically compensate for the reduced amount of sample after each analysis.

In another embodiment of the invention, a "safe" level will be set such that the sample aspiration tube 407 may not travel below a predetermined distance. The "safe" level may be determined at manufacture or may be configurable to reflect the dimension of particular sample reservoirs. This embodiment protects that sample aspiration tube 407 from making contact with the bottom of an empty vessel 802, and in cases in which there is no fluidic sample in a given reaction vessel prevents the sample aspiration tube 407 from moving continuously until the bottom of the vessel 802 is reached and physical damage to the sample aspiration tube 407 and/or the reaction vessel 802 may occur.

In a further embodiment of the invention, if the sample aspiration tube 407 is lowered to the "safe" level without the sensor 702 being triggered, the computerized control system will produce an error message indicating that an aspiration of fluidic sample did not occur. This could be due to several reasons, including but not limited to a vessel 802 not containing any fluidic sample, a clog or plug in the sample aspiration tube 407, or a loss of vacuum. An error message generated will permit the user of the invention to pause the analysis and solve the problem before continuing.

Suitable fluid sensors 702 include optical sensors such as those available from OPTEK Technology of Carrollton, Tex.

In another embodiment, an optical fluid sensor can be fabricated from a light source, two lengths of fiber optics, and an optical detector. One end of the first fiber optic length is coupled with the light source (e.g. a lamp, a red diode laser, and the like). The other end of the first fiber optic length is coupled with a first optical window on the conduit, for example, with optical glue. One end of the second fiber optic length is coupled with a second optical window on the conduit. The other end of the second fiber optic length is coupled with an optical detector, for example, a visible light detector.

Figure 9:
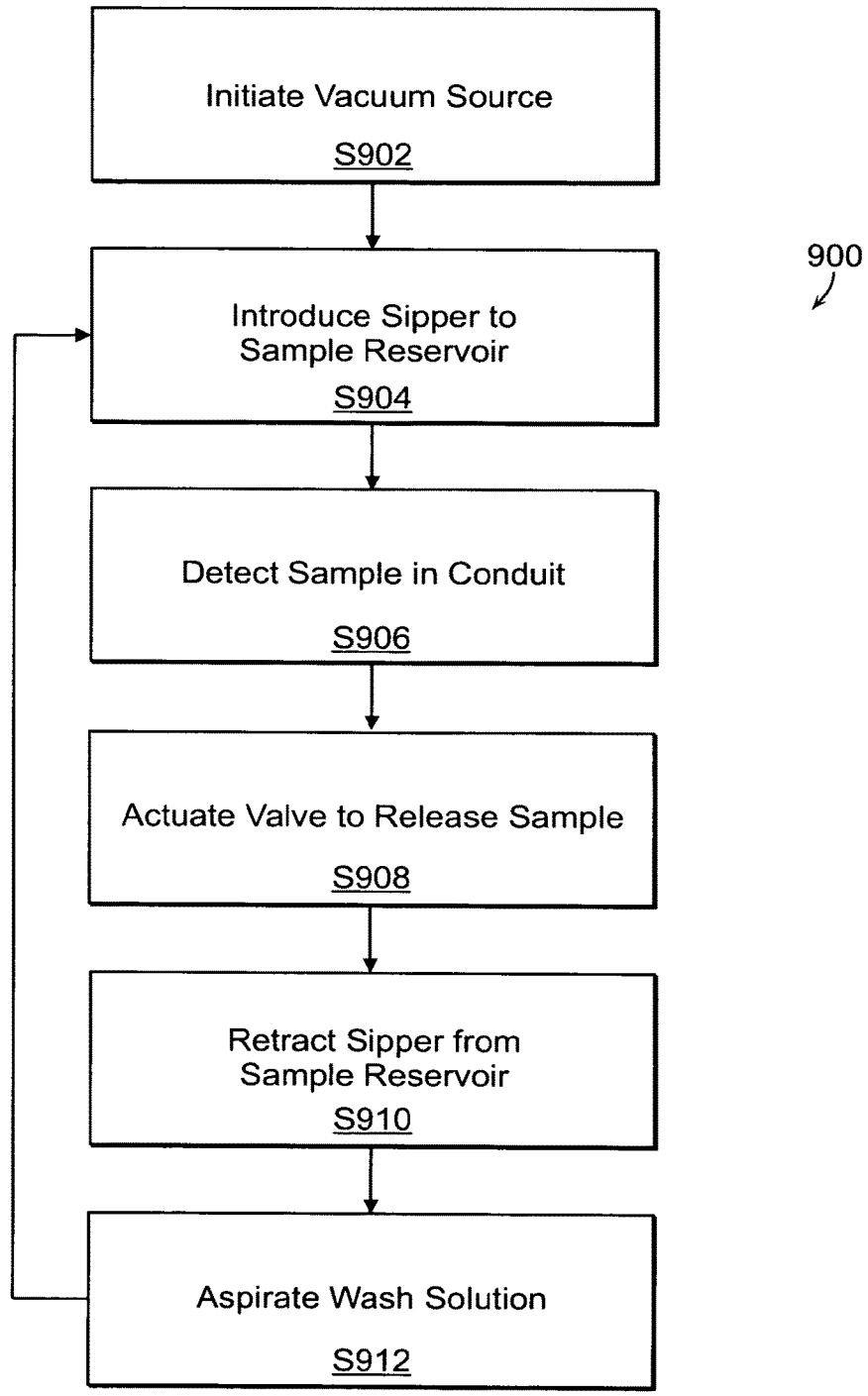
FIG. 9 is a flow chart illustrating the operation of a high-throughput sample injection system, in accordance with an embodiment of the invention.

FIG. 9 is a flowchart depicting the use of the system described herein. In step S902, the vacuum source 211, 411 is initiated. In step S904, sipper aspiration tube 407 is introduced in sample reservoir 401, 802. In step S906, sensor 702 detects a sample in conduit 704. In step S908, valve 405 is actuated to release the sample in injection loop 403. In step S910, sipper aspiration tube S910 is retracted from sample reservoir 401, 802. In step S912, wash solution is aspirate through sample aspiration tube 407 before the process is repeated.

One skilled in the art will appreciate that the steps depicted in FIG. 9 need not necessarily performed sequentially. Rather, certain steps may be performed concurrently, simultaneously, and/or in parallel. For example, sample aspiration tube 407 can be retracted from reservoir 401, 802 while valve 405 is actuated.

Coupling of Mass Spectrometry Devices with Systems Containing Salts or Buffers

Many biological separations use ion-exchange chromatography (e.g. cation exchange or anion exchange) or size-exclusion chromatography. These techniques have particularly important applications in the separations of proteins, peptides, oligonucleotides and many other analytes. The separation techniques have many applications ranging from scientific research and development through the manufacturing of pharmaceutically active compounds.

The techniques typically rely on the selective elution of individual analytes in a complex mixture from a chromatography matrix in response to the variation of one or more biophysical parameters. For example, in cation exchange chromatography, the concentration of cations in the elution buffer is typically increased in a gradual manner. When the concentration of cations in the elution buffer reaches a level at which the affinity of the cations in the elution buffer for the chromatography matrix is stronger than the affinity of the analyte, the analyte is displaced from the chromatography matrix by the cation. The displaced analyte is then eluted from the column. Since different analytes within a complex mixture typically have different affinities for the chromatography matrix a separation can be achieved. Other ion exchange systems rely on a change in pH to enact the desired separation. Many parameters, such as the selection of chromatography matrix, the selection of the cation used in the elution buffer, the rate at which cation concentration is varied, and others may need to be optimized in order to affect a desirable separation.

In size exclusion chromatography (SEC), a separation of analytes is performed based on the relative size of the analytes. Typical SEC separations are performed using a chromatography matrix that consists of porous particles. When a mixture of analytes is introduced on the column, smaller analytes tend to travel through the pores in the chromatography matrix, whereas those analytes that are too large are excluded from the pores and travel through the spaces between the particles. As a result, large particles tend to have a shorter residence time in the chromatography matrix and are eluted early. Smaller particles that travel through the porous matrix have a longer residence on the column and elute later, thereby enacting a size-based separation. As in ion-exchange chromatography, proper selection of the chromatography matrix, buffers used for eluting the sample, the geometry and size of the separation column, and other factors must be optimized to achieve a desirable separation outcome.

Both ion-exchange chromatography and SEC require the presence of salts and/or buffers in the elution fluids. The presence of anions or cations is particularly unavoidable in the case of ion-exchange chromatography where the entire separation is based on the displacement of analytes from the chromatography matrix with an ion. However, even in reversed phase chromatography where the elution is generally performed with an organic solvent and salts are usually not required, there are many cases where the separation may be improved through the addition of certain salts or other compounds to the wash or elution solvents.

Mass spectrometry (MS) is an important analytical technique with applications including research, drug discovery, environmental testing, forensics, quality control, and many others. Mass spectrometry is a mass-selective detector that has the ability to quantitatively detect compounds based on the molecular mass of the analytes. While many different types of mass spectrometry have been described two main basic approaches are often used, namely quadrupole and time-of-flight (TOF). Many variations on both of these approaches, including hybrid systems comprising both approaches, have been developed. In all forms of mass spectrometry, the analytes of interest must be ionized and transferred to the gas phase. There are a large number of different methodologies that have been employed to achieve this, but most modern systems rely on one of two basic approaches. One approach is atmospheric pressure ionization (API), which is further divided into electrospray ionization (ESI) and atmospheric pressure chemical ionization (APCI). The other approach is matrix-assisted laser desorption ionization (MALDI).

The various approaches to MS (quadruopole vs. TOF) and sample ionization (API vs. MALDI) have their various strengths and weaknesses for specific applications. The one constant in all approaches, however, is that MS is not compatible with analytes that are in solutions that contain high ionic strength, such as those that contain high concentrations of salts or buffers. The presence of high concentrations of ions results in a well-documented phenomenon known as ion suppression. Ion suppression causes the analyte of interest to be ionized inefficiently due to the confounding effect of the high concentration of non-specific ions. A second problem with salts and buffers is that many are not volatile. As a result, the salts tend to deposit on the interior surfaces of the MS source region and will degrade instrument performance until eventually the system is no longer operational.

The incompatibility of MS with samples that contain salts and ions together with the need for salts and ions in separation systems such as ion exchange and most size-exclusion chromatography applications means that the two techniques can not be directly interfaced. There are many cases where it is very advantageous to be able to analyze samples separated by ion-exchange or size exclusion chromatography by MS. Currently the only way by which chromatography systems which require salts or buffers can be interfaced with MS is to collect the eluate from the chromatography in fractions. The fractions are then desalted with a secondary separation process that does not require salts, typically a technique using a reversed-phase chromatography system. Since a large number of fractions may be collected to maintain the fidelity of the separation process, the secondary desalting process is typically carried out using a fast system such as solid-phase extraction (SPE) and may be performed in parallel (e.g. with the use of a 96-well SPE plate). It may be necessary to concentrate the eluate from the SPE process to increase the concentration of the analyte(s) to achieve the required sensitivity. The purified, concentrated samples are then analyzed serially with the appropriate MS system. This extends the time and cost associated with the analysis.

One embodiment of the current invention relates to devices and methods which interface a chromatography system that relies on high ionic strength to achieve separation (such as ion-exchange chromatography) with mass spectrometry. The invention provides a direct and fully automated connection between the chromatography system and the MS and eliminates the labor-intensive steps of collecting fractions from the chromatography system, enacting a parallel purification with SPE, sample concentration.

The eluate from the chromatography system is connected to an injection valve. The injection valve is used to capture an aliquot of the eluate from the chromatography system and to divert it to a fast and automated sample purification system, such as the RAPIDFIRE® system, available from BioTrove, Inc. of Woburn, Mass., which has been described U.S. Pat. No. 6,309,600 to Hunter, U.S. Patent Publication 2002/0001544 of Hess, et al., U.S. Patent Publication 2003/0119193 of Hess, et al., U.S. Patent Publication 2005/0123970 of Ozbal, et al., U.S. Pat. No. 6,812,030 to Ozbal, et al., U.S. Pat. No. 6,932,939 to Ozbal, et al., and U.S. Patent Publication 2005/0194318 of Ozbal, et al. The contents of the above patents and publications are each incorporated here in its entirety by reference. The RAPIDFIRE® high throughput mass spectrometry system is capable of solid-phase extraction based purification at throughputs on the order of 5 seconds per sample. With such a system it is possible to take a mass spectrometric reading of the eluate from the chromatography system every 5 seconds. The remaining sample may be collected in fractions for additional analysis or further fractionation.

Figure 10:
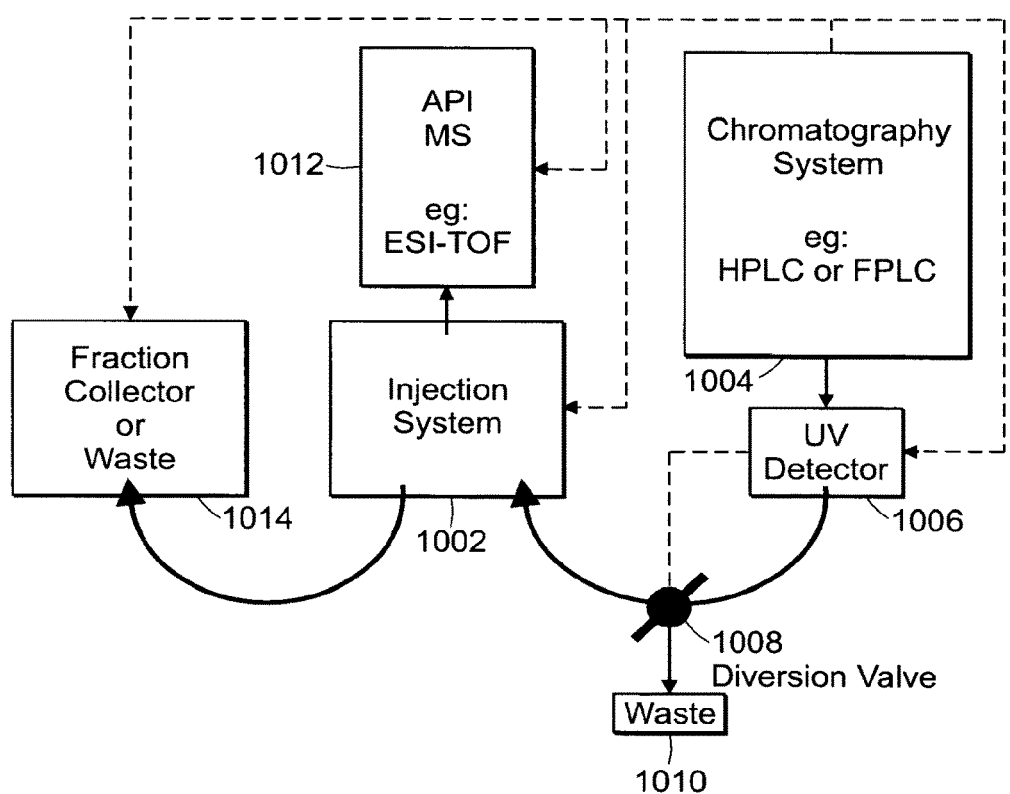
FIGS. 10-11(e) are schematics of a system for coupling a mass spectrometry system and a liquid chromatography system.

The general layout of the system is shown in FIG. 10. An injection system 1002 is directly connected to the chromatography system 1004 (e.g. a high-pressure liquid chromatography system). Optionally, the chromatography system 1002 may have an optical detector 1006 immediately after the chromatography column to monitor and quantify the analytes as they elute from the chromatography column. In one embodiment of the invention, a diversion valve 1008 is placed after the optical detector 1006 that may be used to direct the eluate from the chromatography column away from the downstream instrumentation. The diversion valve 1008 may be electronically controlled by the optical detector 1006 such that if certain signal criteria are met the valve will be actuated. One application of the diversion valve 1008 may be to divert chromatography eluate to waste 1010 if the concentration of analytes is too high in order to protect the injection system 1002 and/or mass spectrometry system 1012 from contamination.

In one embodiment of the invention, starting a separation with the chromatographic system generates a trigger signal (e.g. a TTL (transistor-transistor logic) pulse) that is detected by the injection system, the mass spectrometer, the optical detector, and the fraction collector and is used to synchronize the start of all of the devices. The electronic communication circuitry between the various components of the preferred embodiment of the invention is shown as dashed lines in FIG. 10.

Figure 11A:
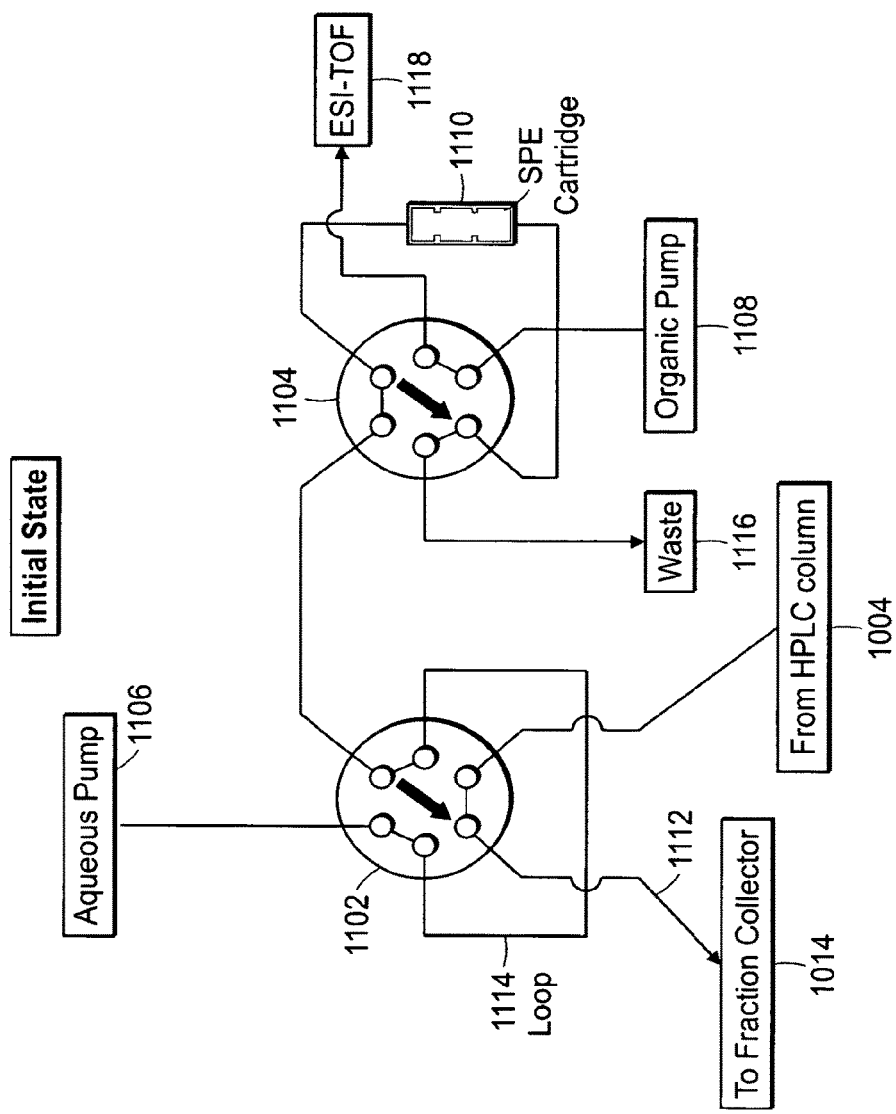

Referring now FIG. 11(a), the invention includes two fluidic injection valves 1102, 1104 and two high pressure fluidic pumps 1106, 1108. The first pump 1102 is used to flow an aqueous wash solution while the second pump 1104 is used to flow an organic elution solution over a SPE cartridge 1110. The details of the SPE cartridge 1112 and its application in sample purification for high-throughput mass spectrometry have been described previously. See, e.g., Nigel J. K. Simpson, *Solid Phase Extraction: Principles, Strategies & Applications* (2000); E. M. Thurman & M. S. Mills, *Solid-Phase Extraction: Principles & Practices* (1998). The eluate from the chromatography system 1004 is connected directly to one port of fluidic injection valve 1102 as shown in FIG. 11(a). Another tube connected to a second port of the same valve 1102 is used to carry the eluate to waste or to a fraction collector 1014, depending on the application. The aqueous fluid from pump 1106 is flowed over the SPE cartridge 1110 in a first direction to condition and equilibrate the cartridge 1110. In the meantime, the organic solvent from pump 1108 is flowed directly to the source of an API-MS to establish a stable spray in ESI or APCI mode. This initial fluidic circuit is shown in FIG. 11(a).

Figure 11B:
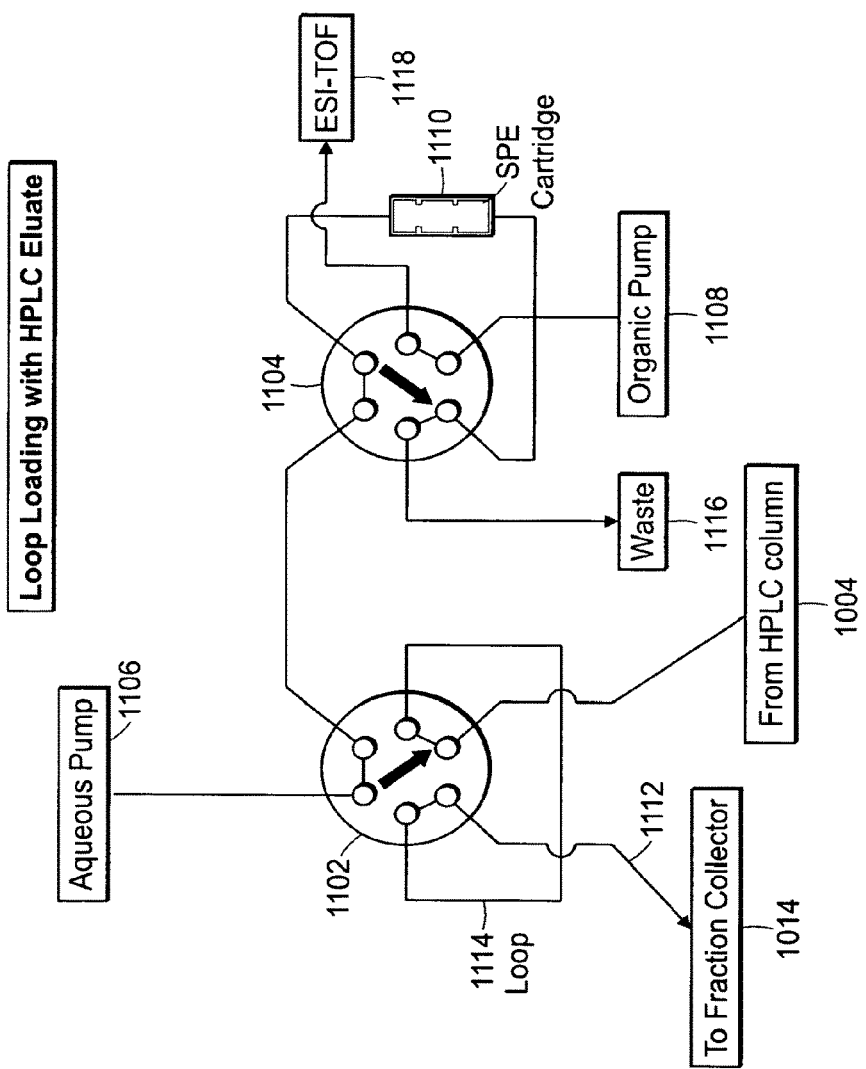

Referring now to FIG. 11(b), once the chromatographic separation is begun, valve 1102 is electromechanically actuated to the position shown in FIG. 11(b). In this position the eluate from the chromatography system 1002 is diverted over an injection loop 1114.

Figure 11C:
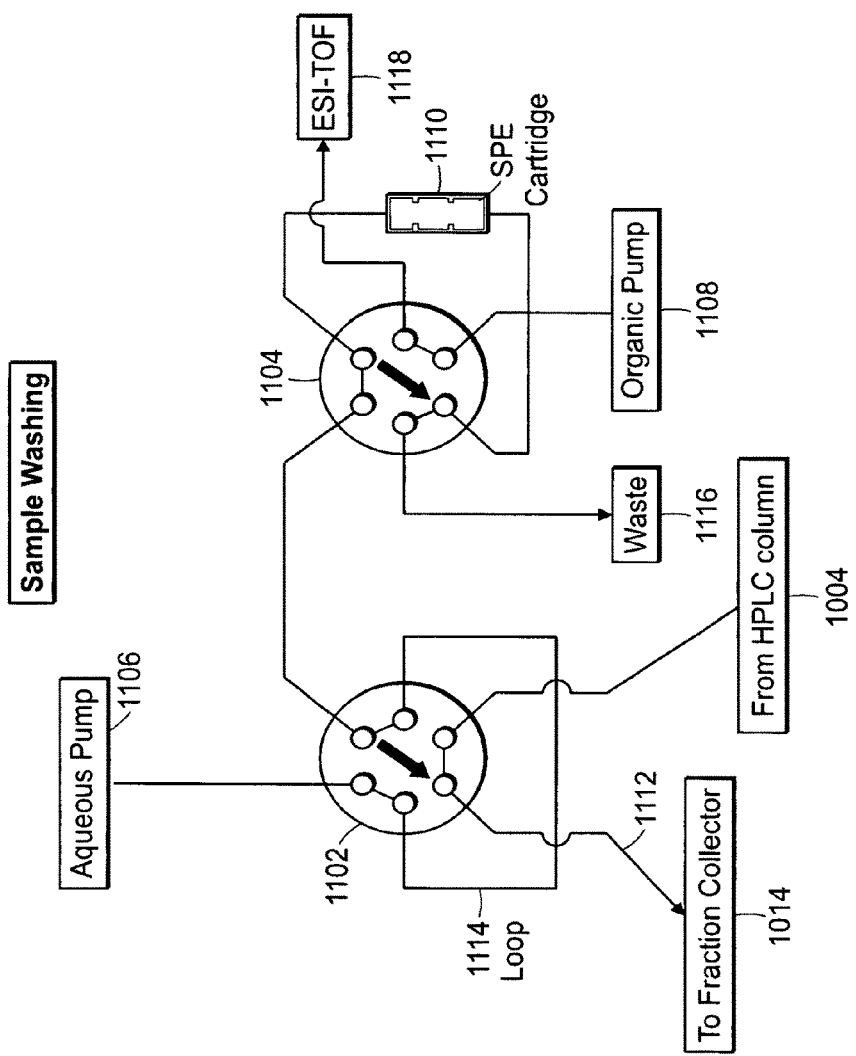

Valve 1102 is actuated a second time to the position shown in FIG. 11(c) after enough time has been allowed to ensure that the injection loop 1114 is completely full of sample. The determination of the amount of time before valve 1102 is actuated the second time can be determined by calculating the flow rate of the chromatography eluate and the volume of the injection loop 1114. For example, if the chromatography solvent is pumped at 0.6 mL/min and a 10 μL injection loop is used, the system will require 1 second to completely fill the injection loop (0.6 mL/min=10 μL/sec). Alternatively, an optical sensor can be coupled with tube 1112 as described above.

Reactuation of valve 1102 after an aliquot of sample has been allowed to fill the loop 1114 as shown in FIG. 11(c) will result in the sample being pushed from the loop 1114 onto the SPE cartridge 1110. The analytes of interest (e.g. proteins or oliginucleotides) will adsorb on the SPE cartridge 1110 while the salts and other ions used in the chromatographic separation will pass through the cartridge 1110 and will be collected in a waste container 1116. Waste container 1116 and 1014 can, in various embodiments, be the same or separate vessels.

Figure 11D:
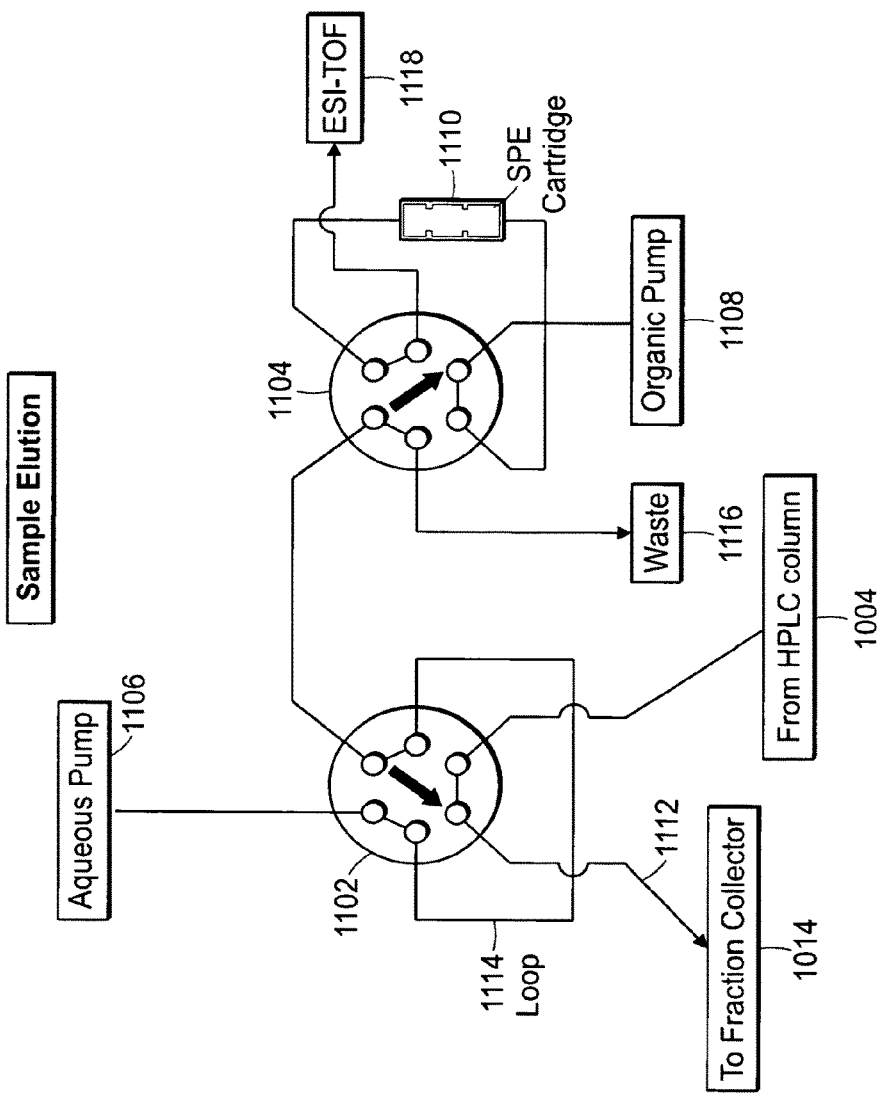

After approximately 10 SPE column volumes of wash solution have been flowed over the SPE cartridge 1110, valve 1104 is actuated to the position shown in FIG. 11(d). In this position, the organic solvent from the second pump 1108 is diverted over the SPE cartridge 1110 in the opposite direction to the sample loading and washing. The purified and desalted analyte(s) of interest are solubilized by the organic solvent, desorbed from the SPE cartridge 1110, and flowed onto the API-MS 1118 for mass spectrometric analysis. Typically, 10 SPE column volumes of organic solvent are sufficient to achieve a near complete elution of analytes. In a preferred embodiment of the invention, the timing of the wash and elution steps adjustable and may be optimized for each specific application. In typical applications, a SPE cartridge with a 4.0 μL column bed volume is used. At a flow rate of 1.2 mL/min (or 20 μL/sec) 10 column volumes of wash or elution solvent can be delivered to the SPE cartridge 1110 in as little as 2 seconds.

Figure 11E:
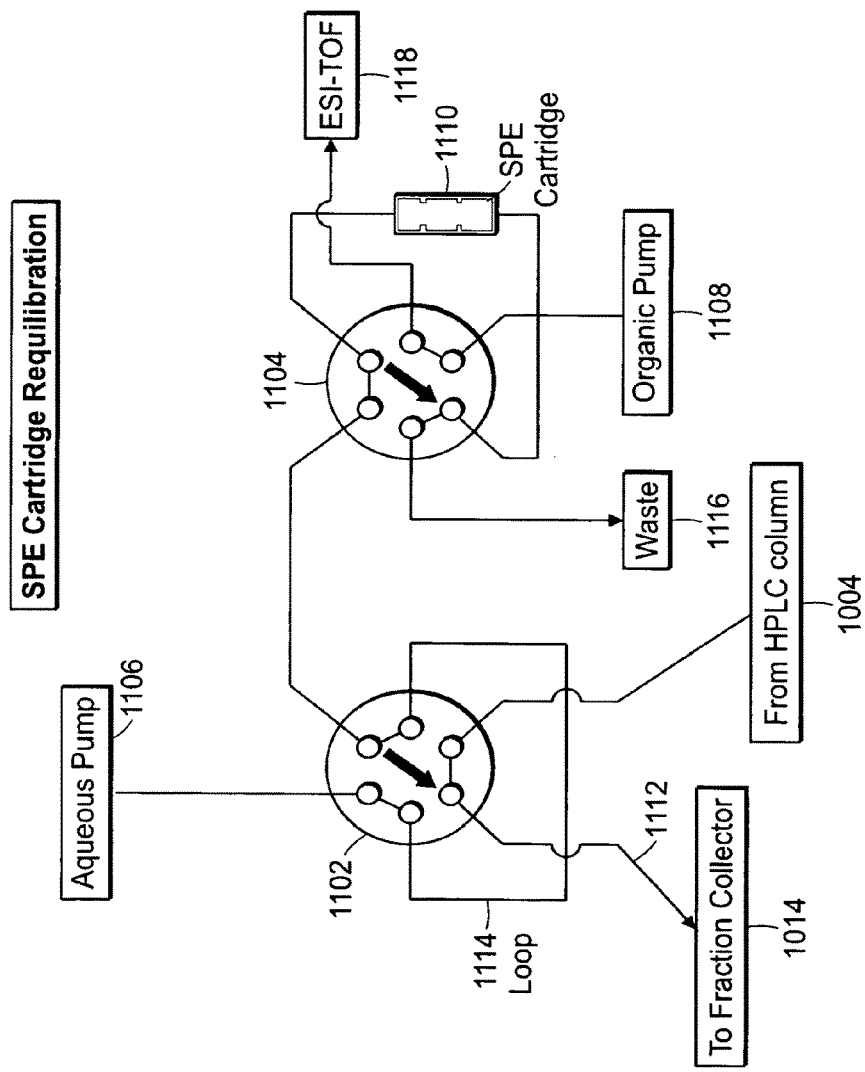

After the analytes have been delivered to the MS 1118, valve 1104 is actuated again to the position shown in FIG. 11(e). This is the initial position of the fluidic system and facilitates the reconditioning and equilibration of the SPE cartridge 1110. In a preferred embodiment of the invention, the cycle shown in FIGS. 11(a) through 11(e) can be repeated at a rate that is selected by the user through a software interface. For example, the user may select a desalting and MS analysis cycle of 10 seconds. Longer cycle times may be selected, however the minimum cycle time will depend on the timing of the valve cycles. Typical peak widths from ion-exchange or size-exclusion chromatography systems are in the 10-30 second range meaning that at least one MS analysis will be available for every peak that is eluted from the chromatography system 1002. Following from the previous example of a 10 μL injection loop and a HPLC flow rate of 0.6 mL/min, 10 μL/sec will be flowed over valve 1102 in the desalting apparatus. If 10 μL of sample is removed via the injection loop at a rate of once per every 10 seconds, a total of 10% of the total eluate from the HPLC column 1002 will be diverted for rapid desalting and MS analysis. The remaining 90% of eluate may be collected in a fraction collector or disposed of in a waste container depending on the application.

At the conclusion of the HPLC experiment, a second electronic signal will direct the injection system 1002, the mass spectrometer 1012, the optical detector 1006, and the fraction collector 1014 to switch to a standby mode. At the end of the chromatographic separation, the user will have a continuous optical trace (such as a UV chromatogram) obtained from the optical detector 1006, a series of non-continuous MS data at the cycling frequency selected, and a series of fractions collected by the fraction collector. There will be an offset between the optical detector and the MS data based on the internal volume of the tubing between the optical detector and the MS source and the wash time selected in the injection system 1002 valving. The offset may be calculated or empirically determined, however, once the offset is known it will be possible to correctly align the MS data with the optical data and the appropriate fraction.

With this invention, it is possible to directly collect MS data from a separation system 1004 that contains MS-incompatible buffers without needing to perform labor intensive and time consuming steps of fraction collection and off-line sample preparation.

Figure 12:
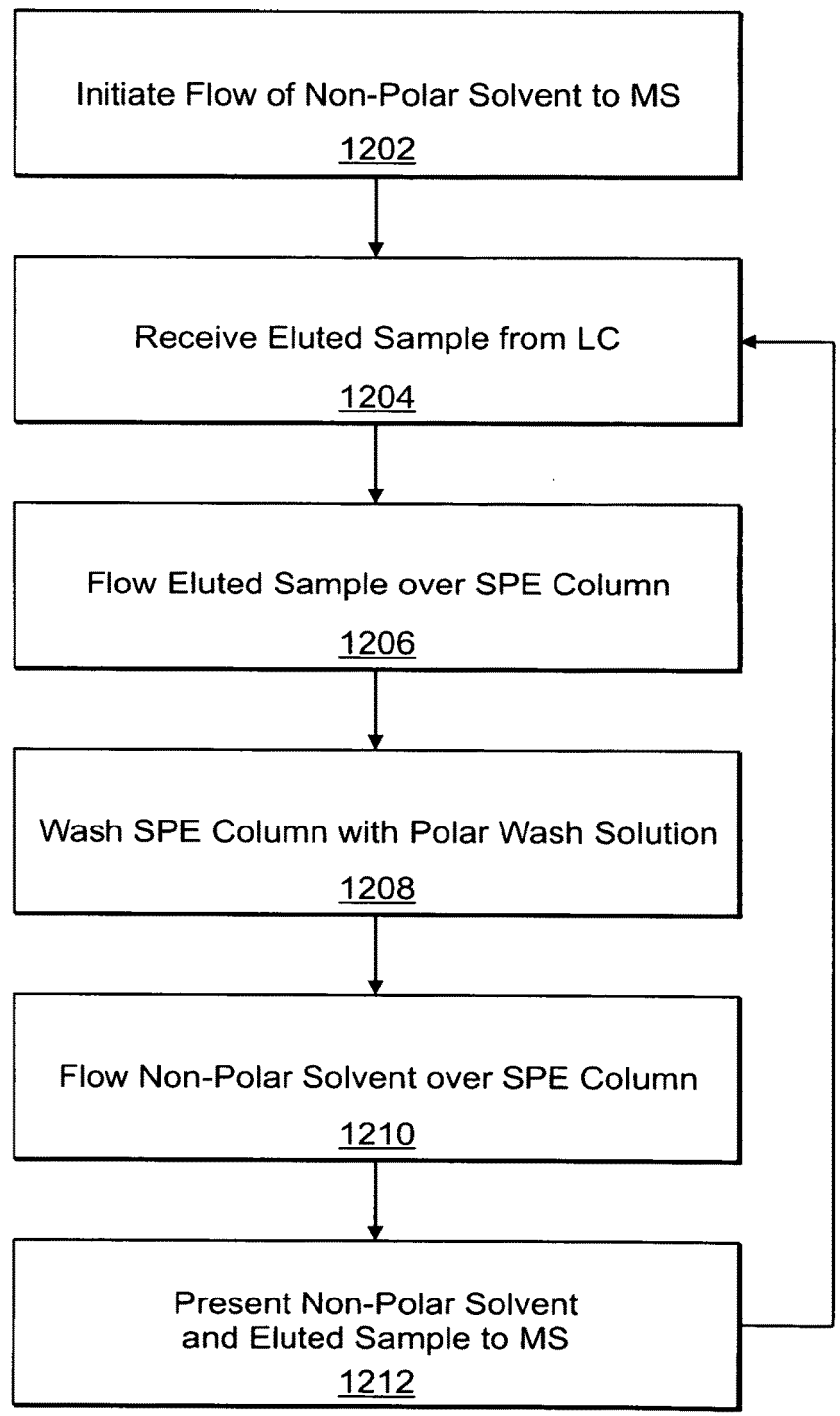
FIG. 12 is a schematic of a method for processing an eluted sample from a liquid chromatography system in a mass spectrometry device

FIG. 12 illustrates a method of processing of an eluted sample from a liquid chromatography system in a mass spectrometry device. In step 1202, a flow of a non-polar solvent to the mass spectrometry device is initiated. In step 1204, an eluted sample is received from the liquid chromatography system. The eluted sample is flowed over an SPE column in step 1206. In step 1208, the SPE column is washed with a polar solution. In step 1210, a non-polar solvent is flowed over the SPE column. In step 1212, the non-polar solvent and the eluted sample are presented to the mass spectrometry device.

The systems and methods described above can also be reversed so such that an eluted sample is non-polar, while the wash solvent is polar. In such an embodiment, the column can be a HILIC (Hydrophilic Interaction Liquid Chromatography) column.

EXAMPLE 4

Cation exchange chromatography is used in the quality control step of the manufacturing of a pharmacologically active protein. For each lot that is manufactured, a 60 minute HPLC separation using an established standard operating procedure must be performed. It is known that the protein of interest elutes off of the HPLC column between 28 and 30 minutes. The entire chromatographic run is monitored by the optical detector 1006 at a wavelength of 220 nm. The HPLC 1004 is run at 0.6 mL/min and a gradient from 0.1 M sodium chloride to 1 M sodium chloride is used to enact the separation.

If any other chromatographic peaks are detected other than the main protein itself it is possible that these are contaminants or breakdown products. Because this protein is meant to be administered to patients, it is required that a full characterization of all potential contaminant peaks be completed before the lot can be approved. Traditionally this characterization would involve collecting fractions from the HPLC, performing a sample preparation step to remove the MS-incompatible salts, and running the MS measurement. Typically, an aliquot of the fraction must also be re-injected in the HPLC separation to ensure that the correct fraction was used in the MS characterization.

The present invention eliminates many of the time consuming and labor intensive steps described above. The device 1002 is placed between the optical detector 1006 and the fraction collector 1014 as shown in FIG. 10. A 10 µL injection loop 1114 is used along with a SPE cartridge 1110 that contains a polymeric matrix with a 4.0 µL bed volume. Pump 1102 is used to deliver a wash solvent consisting of water with 0.02% trifluoroacetic acid while pump 1104 is used to deliver an elution solvent of 80% acetonitrile with 0.02% trifluoroacetic acid. A time of 1 second is selected to completely fill the injection loop 1114, 2 seconds to wash the salts away from the analytes, 2 seconds to elute the analytes off of the SPE cartridge 1110, and 1 second to fully recondition the SPE cartridge 1110. For this application it is decided to run the system at the fastest cycle time, which is 6 seconds.

When the cation exchange HPLC run is initiated, a TTL pulse also triggers the start of the UV detector 1006, the MS 1012, the injection system 1002, and the fraction collector 1014. Over the 60 minute, run a total of 600 high throughput mass spectrometry system cycles will be performed (3600 seconds at 6 seconds/cycle=600 cycles). At the end of the experiment, the MS data, consisting of a time trace with 600 injections can be aligned with the optical detector either through the identification of a landmark (e.g. the main protein in the assay) or through the calculation of the delay within the system. Using the invention described, the equivalent experiment to collecting and preparing 600 individual fractions from the HPLC can be performed in a completely automated fashion and obviate the need for any additional validation experiments.

Multiple Chromatography Columns

Figure 13A:
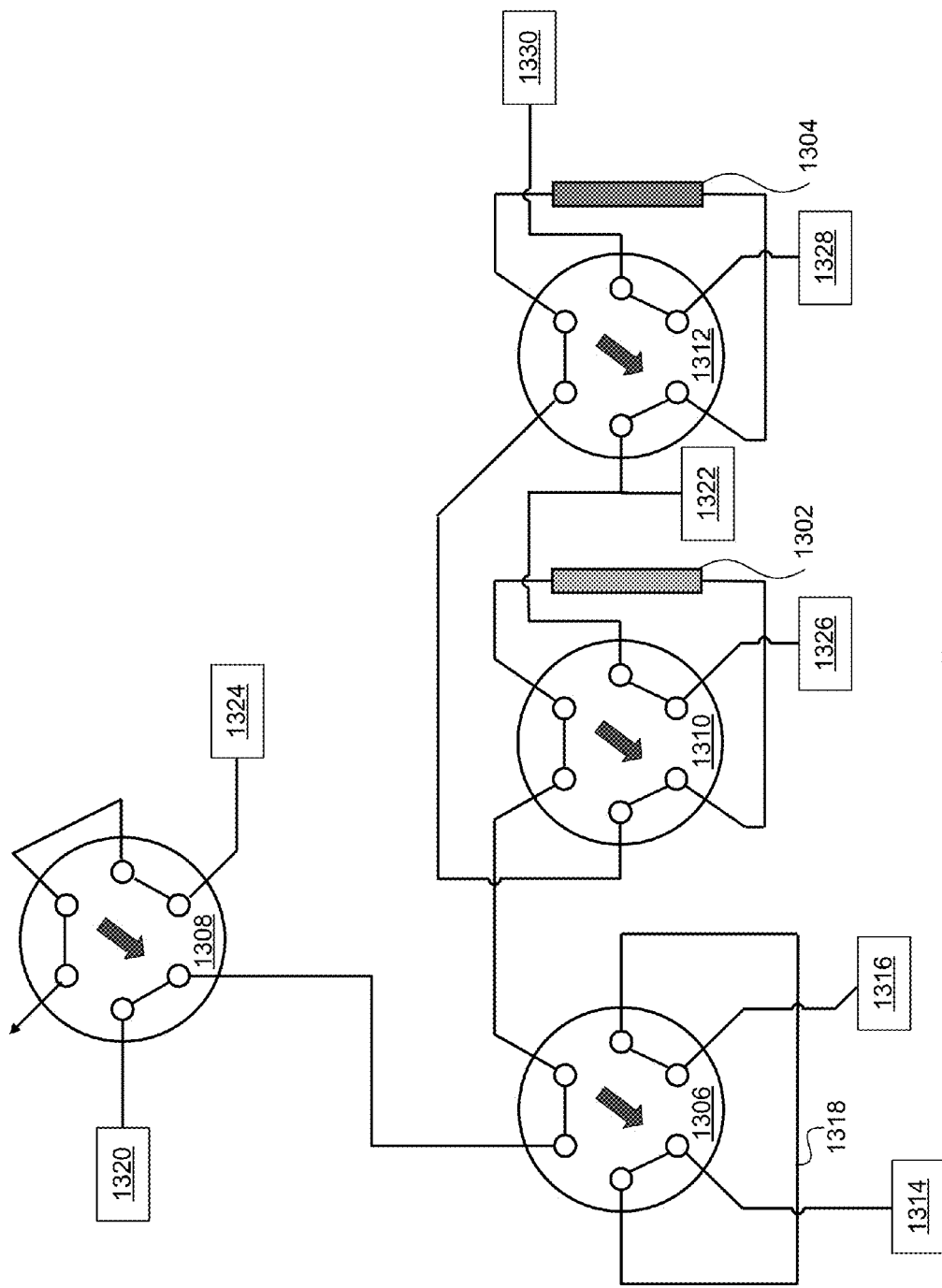
FIGS. 13(a)-13(c) depict an embodiment of the system incorporating two chromatography columns.

Referring now to FIG. 13(a), one embodiment of the invention provides a system 1300 including multiple chromatography columns 1302, 1304.

System 1300 includes a sample injection valve 1306, a wash control valve 1308, a first column control valve 1310, and a second control valve 1312.

In FIG. 13(a), valves 1306, 1308, 1310, 1312 are each actuated to a first position. Sample injection valve 1306 allows vacuum 1316 to draw a sample from sipper 1314 into loop 1318. Wash control valve 1308 permits the flow of an aqueous wash solvent from a first pump 1320 through sample injection valve 1306, to first injection valve 1310, which flows the aqueous wash solvent over the first chromatography column 1302 in a first direction. The aqueous wash solvent continues from the first chromatography column 1302 to the second column control valve 1312, which flows the aqueous wash solvent over the second chromatography column 1304 in a first direction. The aqueous wash solvent then flows to waste 1322.

Figure 13B:
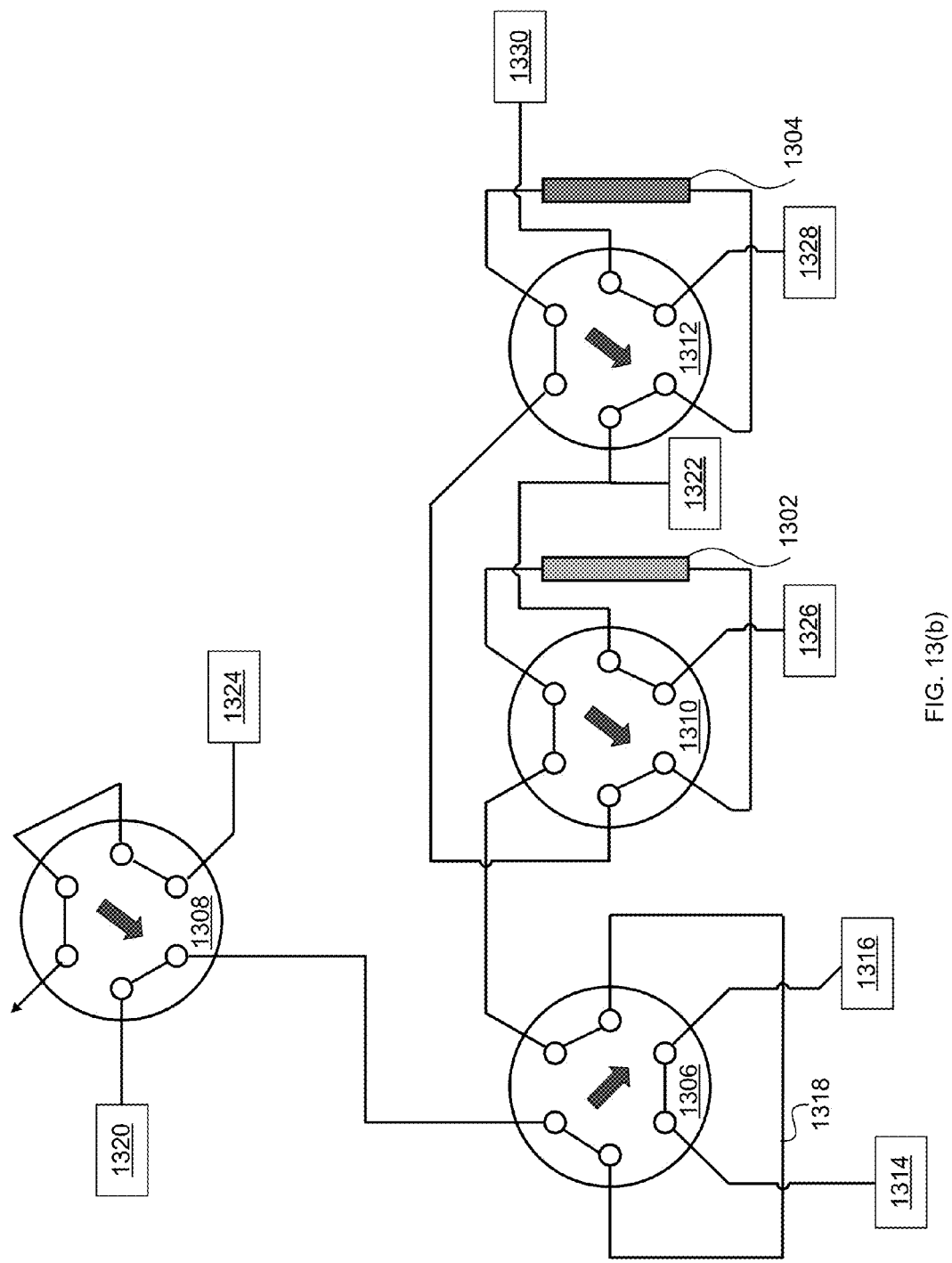

In FIG. 13(b), sample injection valve 1306 is actuated to a second position. Fluid pressure from first pump 1320 pushes the sample loaded onto loop 1318 through the sample injection valve 1306 and the first column control valve 1310, which flows the sample over the first chromatography column 1302 in a first direction to capture undesired components such as phosphorylated compounds. The sample continues from the first chromatography column 1302 to the second column control valve 1312, which flows the non-eluted portion of the sample over the second chromatography column 1304 in a first direction. The non-eluted portion of the sample then flows to waste.

Figure 13C:
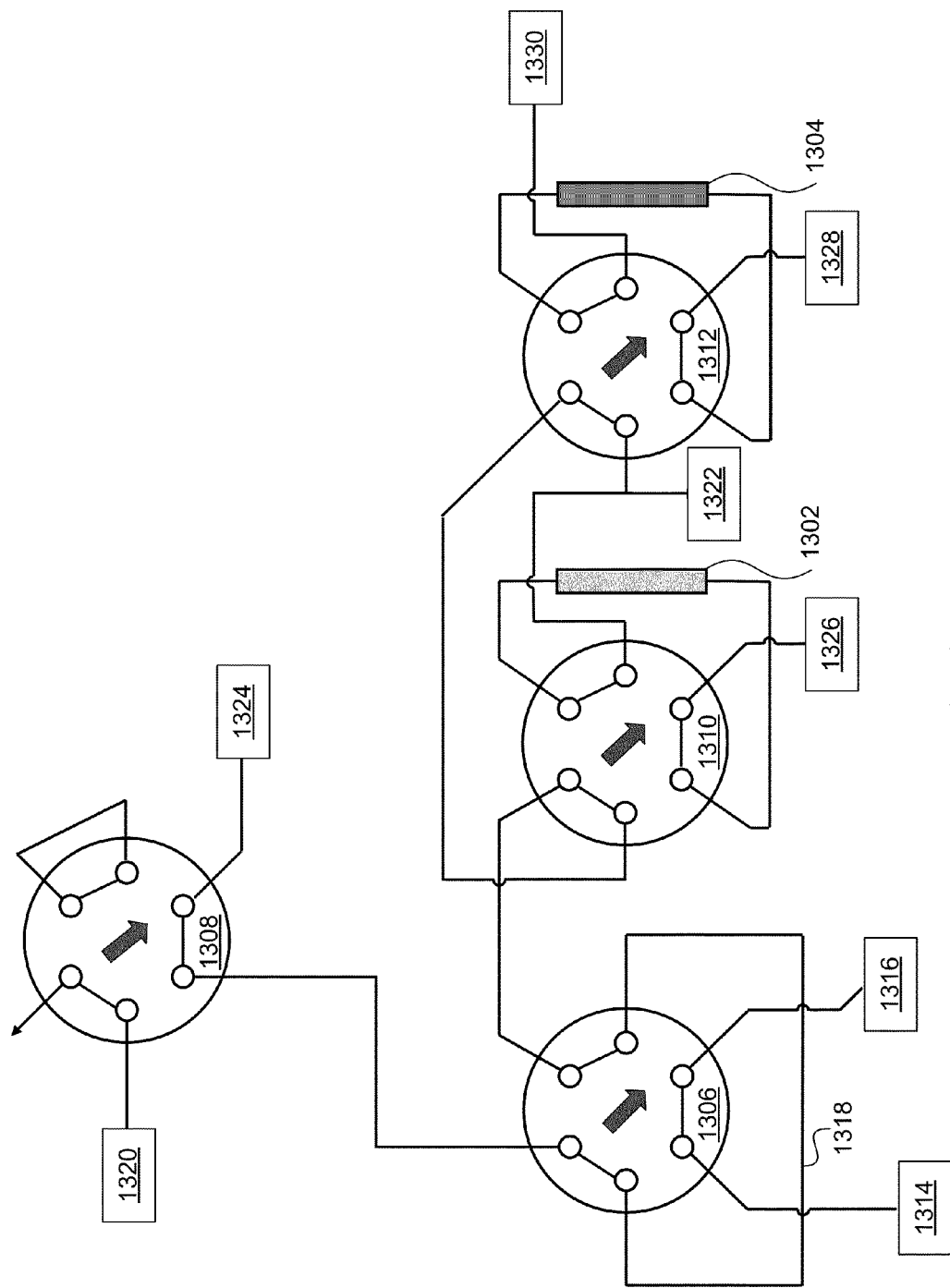

In FIG. 13(c), valves 1306, 1308, 1310, 1312 are each actuated to a second position. Organic elution solvent from a second pump 1324 flows through wash control valve 1308, sample injection valve 1306, sample loop 1318, first column control valve 1310 to waste 1322. Meanwhile, first column control valve 1310 is actuated to deliver an organic elution solvent from third pump 1326 over first chromatography column 1302 in a second direction to elute phospholipids off of first chromatography column 1302 for collection in waste 1322. Second column control valve 1312 is actuated to deliver an organic elution solvent from fourth pump 1328 in a second direction to elute the analytes of interest off of second chromatography column 1304 for presentation to analyzer 1330.

Valves 1306, 1308, 1310, 1312 then return to first positions as depicted in FIG. 13(a) to begin another cycle.

As appreciated from FIGS. 13(a)-13(c), a continuous flow of organic elution solvent from the fourth pump 1328 is provided to analyzer 1330. As discussed herein, this continuous flow maintains a stable ESI or APCI flow and allows constant baseline readings from analyzer 1330 to be obtained.

As discussed herein, the analyzer 1330 can be a mass spectrometry device.

The first chromatography column 1302 can include a matrix with a high affinity for phosphorylated compounds (e.g., phospholipids, phosphopeptides, and the like). Suitable matrices include silica gel, titanium oxide, zirconium oxide, and the like.

The second chromatography column 1304 can be selected from variety of chromatography columns to reflect the characteristics of the analyte(s) of interest. For example, the second chromatography column 1304 can be an ion exchange chromatography column, a cation exchange chromatography column, a hydrophilic interaction chromatography column, a size exclusion chromatography column, and the like.

As discussed herein in the context of FIG. 10, an optical detector and a diversion valve (not depicted) can be positioned between second chromatography column 1304 and analyzer 1330. The diversion valve can be configured for actuation in response to a signal generated by the optical detector in order to protect the sample analyzer from any undesired eluants. System 1300 can also include a fraction collector as discussed herein.

The first, second, and third organic elution solvents can be the same or different solvents. Suitable elution solvents include methyl alcohol, acetonitrile, mixtures thereof, and the like.

In some embodiments, the liquid sample is treated prior to injection with "protein crash" techniques. For example, 20% (v/v) of a 100% (w/v) trichloroacetic acid (TCA) solution can be added to samples. Additionally or alternatively, an organic solvent (e.g., acetonitrile and the like) or a salt (e.g., magnesium sulfate and the like) can be added to the samples. The samples can then be centrifuged to form a pellet of precipitated proteins.

Electronic and Electrical-Mechanical Control

The embodiments of the invention described herein can be controlled by a variety of electronic devices including hardware and software as is known to those of skill in the art. Electrical-mechanical components such as valves 206, 207, 601, 602, 603, 1102, 1104 can be controlled according to interfaces described in related literature can communicate with control devices according to a variety of standard and proprietary technologies and protocols including, but not limited to, transistor-transistor logic (TTL), serial, parallel, FireWire, USB, Ethernet, and the like.

Equivalents

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, computers, clients, servers and the like) depicted as distinct for purposes of illustration may be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein.

Incorporation by Reference

The entire contents of all patents, published patent applications, and other references cited herein are hereby expressly incorporated herein in their entireties by reference.

The invention claimed is:

1. An auto-injection system for high throughput screening of fluidic samples, the system comprising:
    a sample injection valve having:
        i. a first position that applies a reduced pressure to a sample sipper tube for aspirating a fluidic sample into the sample sipper tube, and
        ii. a second position that delivers the fluidic sample to a sample supply loop;
    a first column control valve coupled with a first chromatography column and a source of a first elution solvent, said first column control valve having:
        i. a first position that delivers the fluidic sample from the sample supply loop to said first chromatography column in a first direction, and
        ii. a second position that flows a first elution solvent over said first chromatography column in a second direction; and
    a second column control valve coupled with a sample analyzer, a source of a second elution solvent and a second chromatography column, and configured to facilitate a continuous flow of a second elution solvent to the sample analyzer, said second column control valve having:
        i. a first position that simultaneously delivers the fluidic sample from the sample supply loop to said second chromatography column in said first direction and delivers the second elution solvent to the sample analyzer, and
        ii. a second position that flows the second elution solvent over said second chromatography column in a second direction to deliver the fluidic sample and the second elution solvent to the sample analyzer.

2. The auto-injection system of claim 1, wherein the sample analyzer is a mass spectrometry device.

3. The auto-injection system of claim 1, wherein the first chromatography column has a chromatography matrix selected from the group consisting of: silica gel, titanium oxide matrix, and zirconium oxide matrix.

4. The auto-injection system of claim 1, wherein the second chromatography column is selected from the group consisting of: an ion exchange chromatography column, a cation exchange chromatography column, a hydrophilic interaction chromatography column, and a size exclusion chromatography column.

5. The auto-injection system of claim 1, further comprising an optical detector for analyzing the sample from the second chromatography column.

6. The auto-injection system of claim 1, further comprising: a diversion valve located between the second chromatography column and the sample analyzer.

7. The auto-injection system of claim 6, wherein the diversion valve is configured for actuation in response to a signal generated by the optical detector.

8. The auto-injection system of claim 1, further comprising a fraction collector.

9. The auto-injection system of claim 1, wherein the first elution solvent, the second elution solvent, and the third elution solvent are polar solvents.

10. The auto-injection system of claim 1, wherein the first elution solvent, the second elution solvent, and the third elution solvent are non-polar solvents.

11. The auto-injection system according to claim 1, wherein the first position of said first column control valve further supplies wash buffer solution to wash the first chromatography column.

12. An auto-injection system for high throughput screening of fluidic samples, the system comprising:
  a sample injection valve coupled to a sipper, a vacuum, and a sample loop;
  a wash control valve coupled to the sample injection valve, a first column control valve, a wash buffer solution pump, and a first elution solvent pump;
  a first column control valve coupled to the sample injection valve, a second elution solvent pump, a first chromatography column, and a second column control valve; and
  a second column control valve coupled to the first column control valve, a third elution solvent pump, a second chromatography column, and a sample analyzer;
  wherein the sample injection valve is configured for actuation to:
    a first position, wherein the sample loop is in communication with the vacuum and the sipper to load a sample; and
    a second position, wherein the sample loop is in communication with the wash control valve and the first column control valve;
  wherein the first column control valve is configured for actuation to:
    a first position, wherein the first chromatography column is in communication with the sample injection valve to deliver the sample to the chromatography column in a first direction; and
    a second position, wherein the first chromatography column is in communication with the second elution solvent pump to elute the first chromatography column; and
  wherein the second column control valve is configured to facilitate a continuous flow of an elution solvent to the sample analyzer by actuation to:
    a first position, wherein the second chromatography column is in communication with the first chromatography column via the first column control valve to deliver the unbound contents of said sample to the second chromatography column in a first direction; and
    a second position, wherein the sample analyzer is in communication with the third elution solvent pump via the second chromatography column to flow a third elution solvent over the second chromatography column in a second direction and present the elution solvent and an eluted sample to the sample analyzer; and
  wherein the wash control valve is configured for actuation to:
    a first position, wherein the wash solvent pump is in communication with the sample injection valve; and
    a second position, wherein the first elution pump is in communication with the sample injection valve.

13. A method of processing a sample containing phospholipid, a phosphopeptide, or a mixture thereof for analysis by a mass spectrometry device, the method comprising processing the sample using the sample injection system of any one of claims 1 and 12.

14. The method of claim 13, wherein the sample further comprises salt, buffer, or a mixture thereof.

15. A method for high throughput screening of fluidic samples, the method comprising:
  providing a system including a sample injection valve, a first column control valve, and a second column control valve:
    wherein the sample injection valve is actuatable to:
      i. a first position that applies a reduced pressure to a sample sipper tube for aspirating a fluidic sample into the sample sipper tube, and
      ii. a second position that delivers the fluidic sample to a sample supply loop;
    wherein the first column control valve is in fluid communication with a first chromatography column and the first column control valve having:
      i. a first position that delivers the fluidic sample from the sample supply loop to said first chromatography column in a first direction, and
      ii. a second position that flows a first elution solvent over said first chromatography column in a second direction; and
    wherein the second column control valve is in fluid communication with a sample analyzer and a second chromatography column, and is configured to facilitate a continuous flow of a second elution solvent to the sample analyzer, the second column control valve having:
      i. a first position that simultaneously delivers the fluidic sample from the sample supply loop to said second chromatography column in said first direction and delivers the second elution solvent to the sample analyzer, and
      ii. a second position that flows the second elution solvent over said second chromatography column in a second direction to deliver the fluidic sample and the second elution solvent to the sample analyzer;
  actuating the sample injection valve, the first column control valve, and second column control valve to their first positions to aspirate a fluidic sample into the sample sipper tube;
  actuating the sample injection valve to the second position to deliver the fluidic sample from the sample sipper tube to the sample supply loop and deliver the fluid sample through the first chromatography column and second chromatography column in a first direction; and
  actuating the first column control valve and the second column control valve to their second positions to deliver the first elution solvent over the first chromatography column, and the second elution solvent over the second chromatography column, in the second direction.

16. The method of claim 15, further comprising repeating the actuating steps in a cycle.

17. The method of claim 16, wherein the cycle is performed at a speed of greater than two samples per minute.

18. The method of claim 15, wherein the sample analyzer is a mass spectrometer.

19. The method of claim 15, wherein the sample contains a phospholipid, a phosphopeptide, or a mixture thereof.

20. The method of claim 15, wherein the first chromatography column has a chromatography matrix selected from the group consisting of: silica gel, titanium oxide matrix, and zirconium oxide matrix.

21. The method of claim 15, further comprising preparing the sample by protein precipitation.

22. The method of claim 21, wherein the protein precipitation is performed by adding trichloroacetic acid (100% w/v) to a sample to a concentration of 20% (v/v).

* * * * *

UNITED STATES PATENT AND TRADEMARK OFFICE
CERTIFICATE OF CORRECTION

| | |
|---|---|
| PATENT NO. | : 8,414,774 B2 |
| APPLICATION NO. | : 12/560324 |
| DATED | : April 9, 2013 |
| INVENTOR(S) | : William A. LaMarr et al. |

It is certified that error appears in the above-identified patent and that said Letters Patent is hereby corrected as shown below:

In the Specification

In column 1, line 15, delete "2," and insert -- 22, --, therefor.

Signed and Sealed this
Twelfth Day of November, 2013

Teresa Stanek Rea
*Deputy Director of the United States Patent and Trademark Office*